(12) United States Patent
Nakagomi

(10) Patent No.: US 11,263,763 B2
(45) Date of Patent: Mar. 1, 2022

(54) IMAGE PROCESSING APPARATUS, IMAGE PROCESSING MEHOD, AND STORAGE MEDIUM

(71) Applicant: CANON KABUSHIKI KAISHA, Tokyo (JP)

(72) Inventor: Keita Nakagomi, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 61 days.

(21) Appl. No.: 16/743,972

(22) Filed: Jan. 15, 2020

(65) Prior Publication Data

US 2020/0151889 A1 May 14, 2020

Related U.S. Application Data

(63) Continuation of application No. PCT/JP2018/026693, filed on Jul. 17, 2018.

(30) Foreign Application Priority Data

Jul. 25, 2017 (JP) .............................. JP2017-143687
Jan. 25, 2018 (JP) .............................. JP2018-010523

(51) Int. Cl.
*G06K 9/00* (2006.01)
*G06T 7/38* (2017.01)
*A61B 6/00* (2006.01)
*G06T 7/00* (2017.01)
*G06T 7/33* (2017.01)

(52) U.S. Cl.
CPC ................ *G06T 7/38* (2017.01); *A61B 6/463* (2013.01); *A61B 6/466* (2013.01); *G06T 7/0016* (2013.01); *G06T 7/337* (2017.01); *G06T 2207/10081* (2013.01); *G06T 2207/30012* (2013.01)

(58) Field of Classification Search
CPC ....................................................... G06T 7/38
See application file for complete search history.

(56) References Cited

U.S. PATENT DOCUMENTS

2007/0237290 A1* 10/2007 Mostafavi .............. A61B 6/032
378/21
2009/0279753 A1  11/2009 Sakaida
2010/0231605 A1   9/2010 Moriya
(Continued)

FOREIGN PATENT DOCUMENTS

JP    2007-312838 A    12/2007
JP    2008-6188 A       1/2008
(Continued)

*Primary Examiner* — Oneal R Mistry
(74) *Attorney, Agent, or Firm* — Canon U.S.A., Inc. IP Divsion

(57) ABSTRACT

An image processing apparatus obtains segment definition information that defines a plurality of segments obtained by dividing a human body along a body axis, and obtains a three-dimensional image including a plurality of slice images indicating cross sections of a subject. The image processing apparatus identifies, based on the segment definition information, a segment to which a cross section corresponding to at least one slice image among the slice images included in the image belongs, and calculates a coordinate value of the at least one slice image, based on the identified segment and a reference coordinate system in which a coordinate value is defined for each of the segments.

14 Claims, 10 Drawing Sheets

(56) References Cited

U.S. PATENT DOCUMENTS

| | | | | |
|---|---|---|---|---|
| 2013/0322717 | A1* | 12/2013 | Bar-Shalev | G06T 7/74 |
| | | | | 382/131 |
| 2014/0241511 | A1* | 8/2014 | Hausotte | A61B 5/103 |
| | | | | 378/206 |
| 2017/0372473 | A1* | 12/2017 | Ujiie | G06F 3/0482 |

FOREIGN PATENT DOCUMENTS

| JP | 2008-43524 A | 2/2008 |
|---|---|---|
| JP | 4818846 B2 | 11/2011 |
| JP | 2015-171456 A | 10/2015 |

* cited by examiner

IMAGE PROCESSING APPARATUS, IMAGE PROCESSING MEHOD, AND STORAGE MEDIUM

CROSS-REFERENCE TO RELATED APPLICATIONS

This application is a Continuation of International Patent Application No. PCT/JP2018/026693, filed Jul. 17, 2018, which claims the benefit of Japanese Patent Application No. 2017-143687, filed Jul. 25, 2017, and Japanese Patent Application No. 2018-010523, filed Jan. 25, 2018, all of which are hereby incorporated by reference herein in their entirety.

TECHNICAL FIELD

The present invention relates to an image processing apparatus, an image processing method, and a storage medium.

BACKGROUND ART

In the medical field, diagnoses are performed using three-dimensional images obtained by various image capturing devices (modalities) such as computed tomography devices (hereinafter referred to as CT devices). In particular, to capture changes in the state of a subject over time, images captured at different points in time are compared. The images can be easily compared by displaying a slice in one of the images and a slice (hereinafter referred to as a corresponding slice) in another image, both slices including substantially the same anatomical structure, side by side. The term "slice" refers to an image for a cross section extracted from a three-dimensional image. To facilitate comparison of images, each slice in one of the images to be compared is associated with the corresponding slice in the other image in advance, the images being captured at different points in time. The term "aligning", as used herein, refers to the act of associating each of slices constituting a three-dimensional image with a slice or slices (a corresponding slice or slices) in another or other three-dimensional images including substantially the same anatomical structure as the anatomical structure of the slice.

A plurality of images are used for a diagnosis, and each of the images often has a large number of slices (several hundred or more). If individual slices are aligned manually, a heavy load may be imposed on the operator.

In light of the issue described above, PTL 1 discloses a method for aligning images captured at a plurality of points in time by using a reference coordinate system having coordinate values, each of which is related to an anatomical position, such that even when three or more images are to be compared, the images can be easily aligned. However, if images to be aligned have different balances of sizes of an anatomical structure between anatomical positions, slices having the same coordinate value in the reference coordinate system may not be located at corresponding positions in the images. One method to address this issue is also disclosed in PTL 1. In the disclosed method, a plurality of coordinate systems are created in accordance with the sizes of anatomical structures (by bone structure, age, height, sex, and so on), and a suitable coordinate system is selected for each image being processed to achieve more accurate alignment.

CITATION LIST

Patent Literature

PTL 1 Japanese Patent No. 4818846

As described above, in the technique described in PTL 1, when a single reference coordinate system is used, slices in different images may not be correctly aligned if the images have different balances of sizes of an anatomical structure of a subject. In addition, to address this issue and achieve more accurate alignment, a coordinate system needs to be selected for use from among the plurality of coordinate systems.

Accordingly, the present invention provides an image processing apparatus, an image processing method, and a program that enable accurate alignment using a reference coordinate system having coordinate values, each of which is related to an anatomical position.

One of other objects disclosed herein is to achieve advantages that are derived from configurations described in the following description of embodiments below and that are not achievable in the related art.

SUMMARY OF INVENTION

An image processing apparatus according to an aspect of the present invention includes information obtaining means for obtaining segment definition information that defines a plurality of segments obtained by dividing a human body along a body axis, image obtaining means for obtaining a three-dimensional image including a plurality of slice images indicating cross sections of a subject, segment identifying means for identifying, based on the segment definition information, a segment to which a cross section corresponding to at least one slice image among the slice images included in the image belongs, and coordinate value calculating means for calculating a coordinate value of the at least one slice image, based on the identified segment and a reference coordinate system in which a coordinate value is defined for each of the segments.

Further features of the present invention will become apparent from the following description of exemplary embodiments with reference to the attached drawings.

DESCRIPTION OF EMBODIMENTS

The following describes embodiments of the present invention as illustrative examples in detail with reference to the drawings. It is noted that the components described in the embodiments are for illustrative purposes only and that the technical scope of the present invention is defined by the claims, but is not limited by the following individual embodiments.

First Embodiment

An image processing apparatus according to a first embodiment is an apparatus that displays a plurality of three-dimensional images. The apparatus has a function of computing a coordinate value of each of slices in an input image in a coordinate system (reference coordinate system) having coordinate values, each of which is defined for a position having an anatomical feature, such that corresponding slices in different three-dimensional images are aligned and displayed. The apparatus has a feature of separating anatomical structures of a human body into a plurality of segments along the body axis in a process of determining a coordinate value of each slice in the reference coordinate system, and computing a coordinate value of each slice for each of the segments by using information on the segment.

The technique described above normalizes the positions of the anatomical structures of the human body for each site along the body axis, thereby absorbing different balances of sizes of the anatomical structures (individual difference). Accordingly, it is possible to provide more accurate alignment results to a user in a process of aligning different images.

Figure 1:
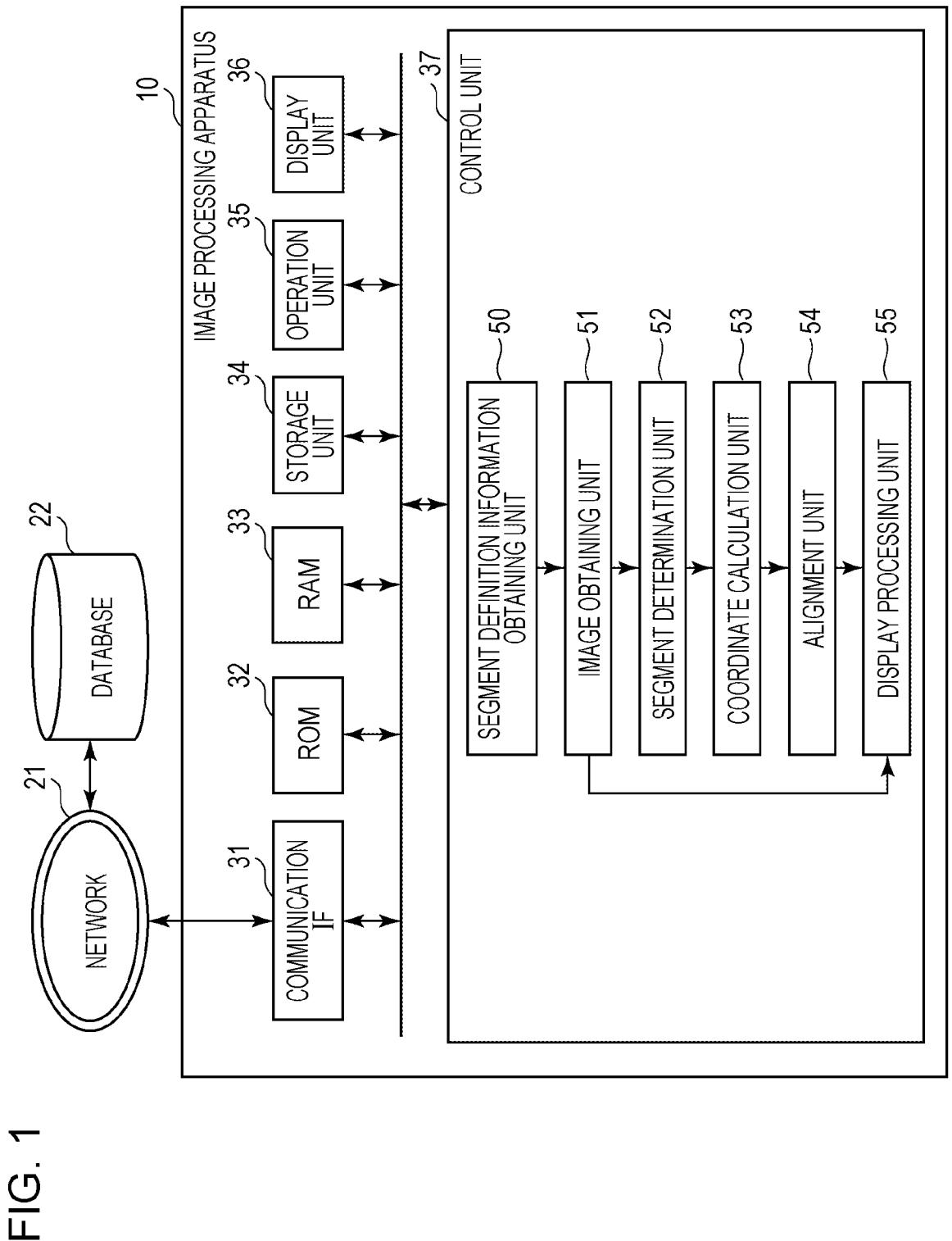
FIG. 1 illustrates a functional configuration of an image processing apparatus according to a first embodiment.

The following describes the configuration and operation of the image processing apparatus according to this embodiment with reference to FIG. 1. FIG. 1 is a block diagram illustrating an example configuration of an image processing system (also referred to as a medical image processing system) including the image processing apparatus according to this embodiment. The image processing system includes, as its functional components, an image processing apparatus 10, a network 21, and a database 22. The image processing apparatus 10 is communicably connected to the database 22 via the network 21. The network 21 includes, for example, a local area network (LAN) or a wide area network (WAN).

The database 22 stores and manages images of a subject and information associated with the images. The image processing apparatus 10 is capable of obtaining an image stored in the database 22 via the network 21. The image processing apparatus 10 includes a communication interface (IF) 31 (communication unit), a read-only memory (ROM) 32, a random access memory (RAM) 33, a storage unit 34, an operation unit 35, a display unit 36, and a control unit 37.

The communication IF 31 (communication unit) is constituted by a LAN card or the like and is configured to establish communication between an external device (e.g., the database 22) and the image processing apparatus 10. The ROM 32 is constituted by a non-volatile memory or the like and is configured to store various programs. The RAM 33 is constituted by a volatile memory or the like and is configured to temporarily store various kinds of information as data. The storage unit 34 is constituted by a hard disk drive (HDD) or the like and is configured to store various kinds of information as data. The operation unit 35 is constituted by a keyboard, a mouse, a touch panel, or the like and is configured to input instructions given from the user (such as a doctor) to various devices.

The display unit 36 is constituted by a display or the like and is configured to display various kinds of information to the user. The control unit 37 is constituted by a central processing unit (CPU) or the like and is configured to control the overall operation of the image processing apparatus 10. The control unit 37 includes, as its functional components, a segment definition information obtaining unit 50, an image obtaining unit 51, a segment determination unit 52, a coordinate calculation unit 53, an alignment unit 54, and a display processing unit 55.

The segment definition information obtaining unit 50 obtains segment definition information from the database 22. The segment definition information is information for dividing the human body into a plurality of segments along the body axis on the basis of anatomically characteristic cross sections including predetermined anatomical features of the human body. That is, the segment definition information obtaining unit 50 corresponds to an example of information obtaining means for obtaining segment definition information that defines a plurality of segments obtained by dividing a human body along a body axis. The term "anatomically characteristic cross section", as used herein, refers to a cross section on which an anatomical feature appearing at or near a boundary position of a set of anatomical structures (such as sites) is delineated when, for example, the anatomical structures are seen along the body axis of the human body. That is, all the anatomical structures are separated into a plurality of kinds of sites (corresponding to the segments described above) along the body axis by using the anatomically characteristic cross sections. The locations of the anatomically characteristic cross sections and the number of anatomically characteristic cross sections, that is, the number of segments obtained as a result of division, may be read from the database 22 in which such information is stored in advance. Alternatively, information input by the user through the operation unit 35 may be used.

The image obtaining unit 51 obtains from the database 22 two or more images (images I1, I2, . . . , and IN, where N is the total number of images) to be aligned. That is, the image obtaining unit 51 corresponds to an example of image obtaining means for obtaining a three-dimensional image including a plurality of slice images indicating cross sections of a subject. These images are three-dimensional images of a subject, which are captured by various modalities. In this embodiment, the images are CT images, by way of example but not limitation. These images may be other types of images. The present invention is applicable to any three-dimensional image, regardless of the type of the image. The plurality of images may be any images to be compared. That is, the images may be captured images of the same subject or captured images of different persons such as a healthy person and a patient.

The segment determination unit 52 determines to which of the plurality of segments at least one slice in each of the images to IN belongs. That is, the segment determination unit 52 corresponds to an example of segment identifying means for identifying, based on the segment definition information, a segment (hereinafter referred to as a belonging segment) to which a cross section corresponding to at least one slice image included in an image belongs. The determination of a belonging segment may be implemented through estimation processing or the like using information obtained by the segment definition information obtaining unit 50, information on pixel values in the slice, and information on a feature value.

The coordinate calculation unit 53 calculates, based on information on the belonging segment determined by the segment determination unit 52, the coordinate value of the slice image in a reference coordinate system corresponding to the belonging segment. That is, the coordinate calculation unit 53 corresponds to an example of coordinate value calculating means for calculating a coordinate value of a slice image, based on the identified segment and a reference coordinate system in which a coordinate value is defined for each segment.

The alignment unit 54 calculates positions of corresponding slices in the images I1 to IN on the basis of the coordinate value calculated by the coordinate calculation unit 53. In other words, the alignment unit 54 aligns the images I1 to IN. That is, the alignment unit 54 corresponds to an example of association means for associating slice images having substantially the same coordinate value in the reference coordinate system, each of the slice images being included in one of the plurality of obtained images.

The display processing unit 55 displays, in an image display area of the display unit 36, at least two or more images among the input images I1 to IN in such a manner as to facilitate comparison of corresponding slices in the two or more images on the basis of the results calculated by the alignment unit 54.

The components of the image processing apparatus 10 described above function in accordance with a computer program. For example, the control unit 37 (CPU) uses the RAM 33 as a work area, and reads and executes a computer program stored in the ROM 32, the storage unit 34, or the like to implement the respective functions of the components. The functions of some or all of the components of the image processing apparatus 10 may be implemented by using dedicated circuitry. Alternatively, the functions of some of the components of the control unit 37 may be implemented by using a cloud computer.

For example, a computing device in a different location from the image processing apparatus 10 may be communicably connected to the image processing apparatus 10 via the network 21, and the image processing apparatus 10 and the computing device may transmit and receive data to and from each other to implement the functions of the components of the image processing apparatus 10 or the control unit 37.

Next, an example of the operation of the image processing apparatus 10 illustrated in FIG. 1 will be described with reference to FIGS. 2 to 7.

Figure 2:
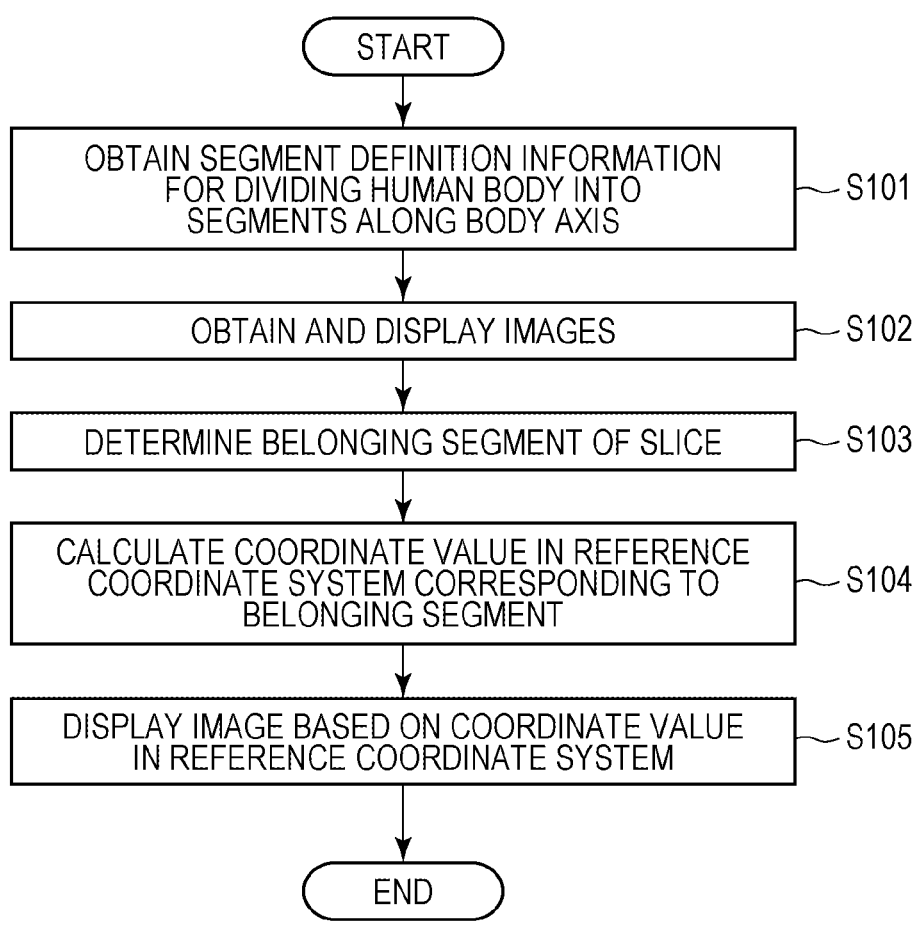
FIG. 2 is a flowchart illustrating an example operation procedure of the image processing apparatus.

FIG. 2 is a flowchart illustrating an example operation procedure of the image processing apparatus 10. While this embodiment describes an example based on anatomical features of the bone, this embodiment is also applicable when any other site of interest is set.

Step S101: Obtaining of Segment Definition Information for Dividing Human Body into Segments Along Body Axis In step S101, in response to an instruction given from the user through the operation unit 35 to start image processing, the segment definition information obtaining unit 50 obtains from the database 22 segment definition information for separating anatomical structures of a human body into a plurality of segments along the body axis, and stores the segment definition information in the RAM 33.

Figure 3:
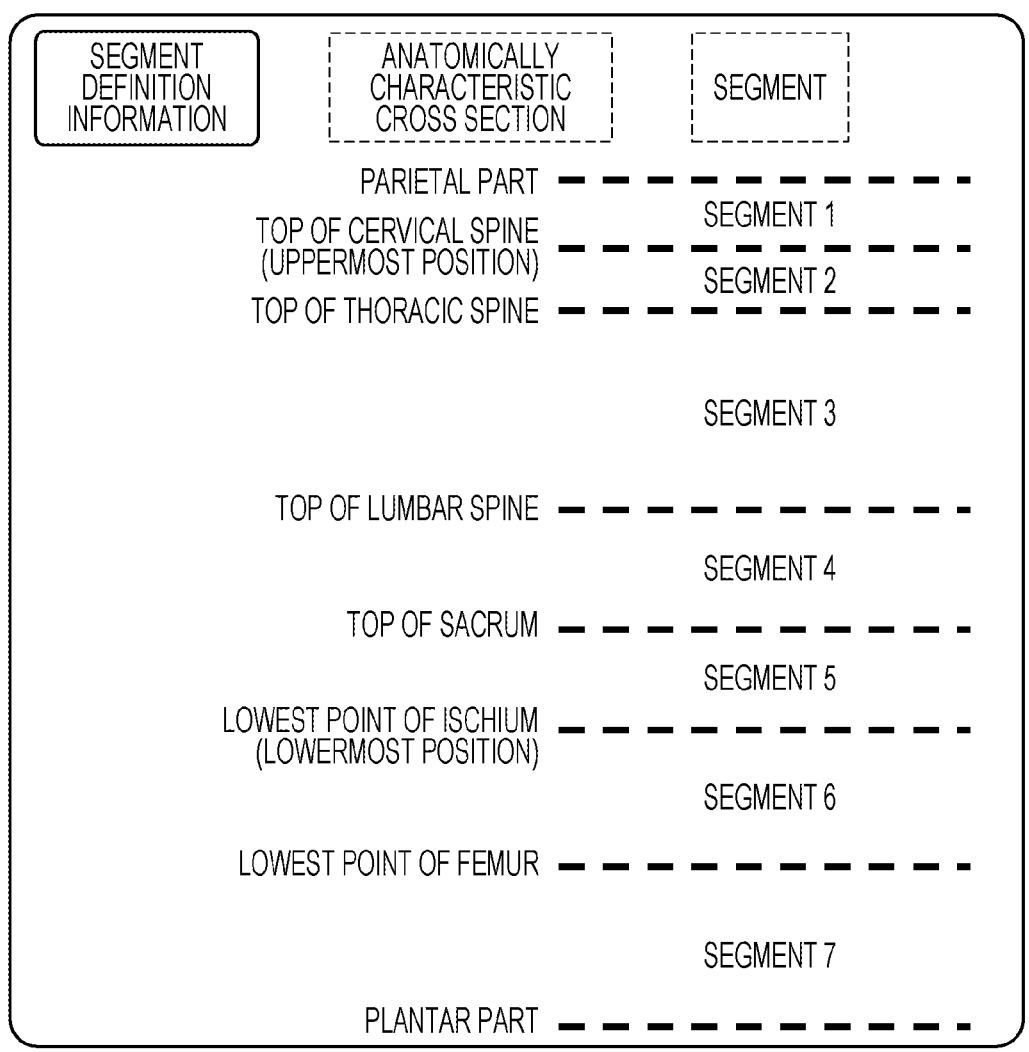
FIG. 3 illustrates an example of segment definition information obtained by a segment definition information obtaining unit.

The segment definition information includes information on the positions of a plurality of anatomically characteristic cross sections and information on segments separated by the cross sections. An example of the segment definition information is illustrated in FIG. 3. In FIG. 3, the body from the parietal part to the plantar part is divided into seven segments, namely, segments 1 to 7, by way of example, using information on the bone structure of the human body (such as a cross section at the uppermost position among cross sections of the cervical spine, a cross section at the uppermost position among cross sections of the thoracic spine, and a cross section at the uppermost position among cross sections of the lumbar spine). More specifically, the segment 1 represents a region from the parietal part to the position of the slice of the uppermost cervical vertebra, and the segment 2 represents a region from the position of the slice of the uppermost cervical vertebra to the position of the slice of the uppermost thoracic vertebra. Also for the remaining segments to the segment 7 representing a region from the underside of the femur to the plantar part, the human body is divided into segments along the body axis on the basis of cross sections indicating anatomical features. The anatomically characteristic cross sections used for segmentation are not limited to those in the illustrated example, and cross sections based on the positions of other organs may be used.

Step S102: Obtaining and Display of Images

Figure 4:
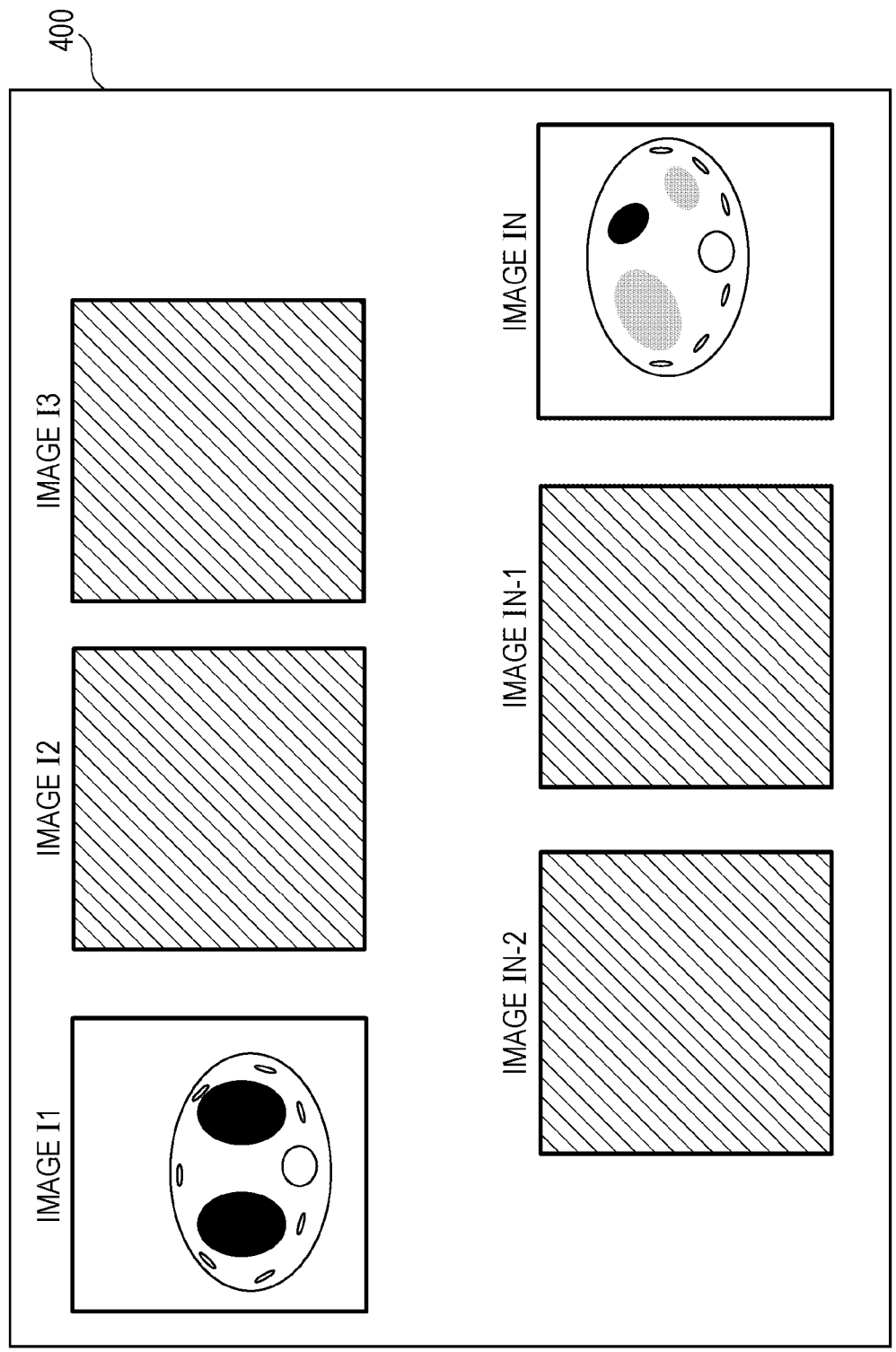
FIG. 4 illustrates an example of images obtained by an image obtaining unit and displayed on a display unit.

In step S101, in response to an instruction given from the user through the operation unit 35 to obtain images (I1 to IN), the image obtaining unit 51 obtains the images I1 to IN, which are designated by the user, from the database 22, and stores the images I1 to IN in the RAM 33. Further, as illustrated in FIG. 4, the display processing unit 55 displays the images obtained from the database 22 in an image display area 400 of the display unit 36. The following describes an example in which the images I1 to IN are assumed to have substantially the same image range (from the top of the cervical spine to the lowest point of the ischium). However, the images I1 to IN need not have the same image range, and may have different image ranges. The process of displaying the images obtained from the database 22 on the display unit 36 by the display processing unit 55 may be omitted. Further, if the image obtaining unit 51 does not obtain a plurality of images (i.e., the image obtaining unit 51 obtains a single image) in step S101, the processing of step S103 and the following steps may not be executed. In other words, the processing of step S103 and the following steps may be executed if the image obtaining unit 51 obtains a plurality of images. That is, the processing of step S103 and the following steps corresponds to an example of segment identifying means for identifying a segment to which a cross section corresponding to a slice image belongs in response to obtaining of a plurality of images.

Step S103: Determination of Belonging Segment of Each Slice in Each Image

In step S103, the segment determination unit 52 determines a segment to which each of slices constituting each of the images I1 to IN belongs among a plurality of segments included in the segment definition information, and stores the determined segment in the RAM 33.

Figure 5:
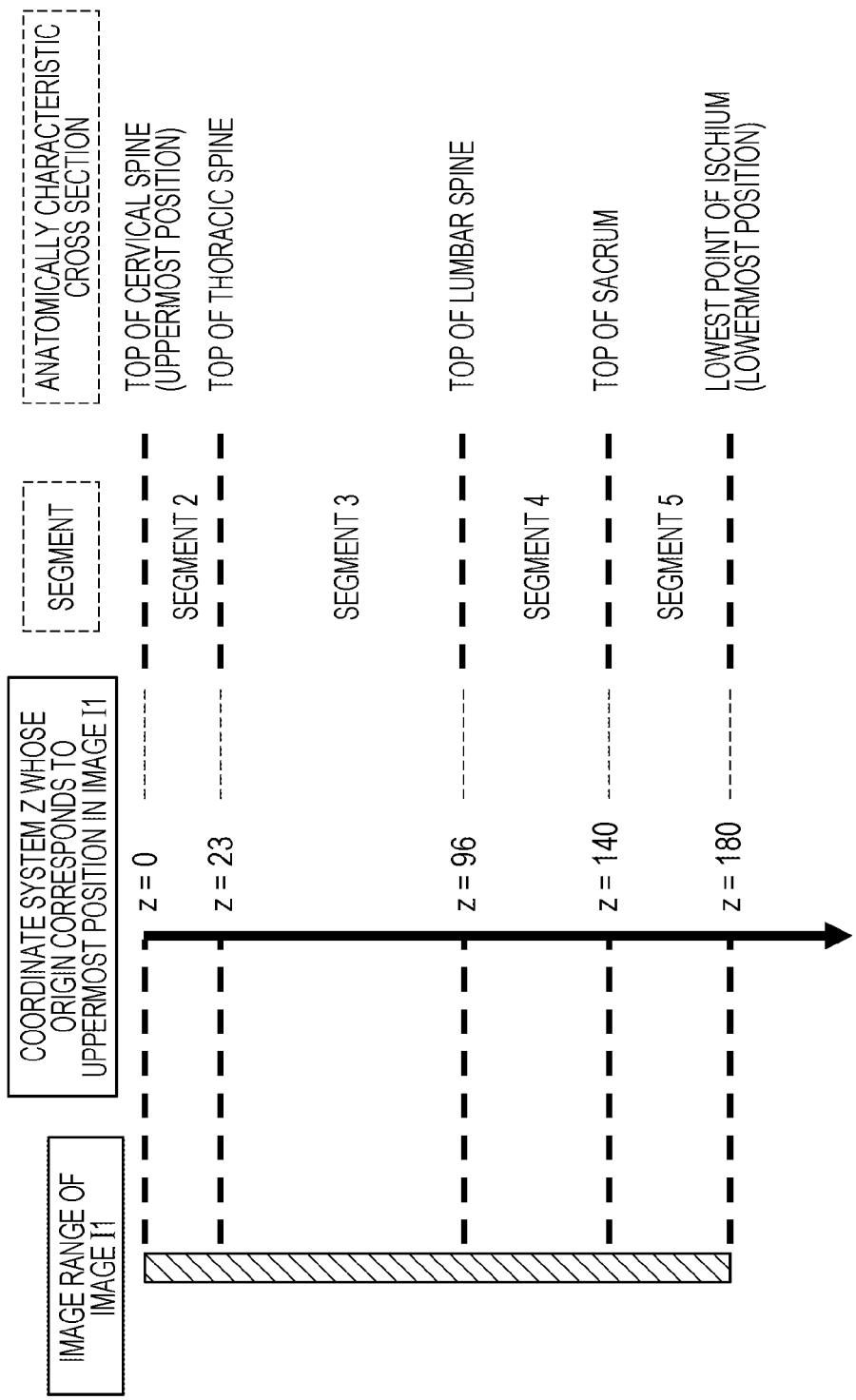
FIG. 5 illustrates an image I1 including slices starting from the slice of the top of the cervical spine to the slice of the lowest point of the ischium.

By way of example, as illustrated in FIG. 5, the image I1 includes 181 slices representing the region from the top of the cervical spine to the lowest point of the ischium. In the example illustrated in FIG. 5, a coordinate system Z whose origin corresponds to the uppermost position in the image I1 is defined, in which the slice at the uppermost position among the slices in the image I1 is denoted by $z=0$ and the slice at the next uppermost position is denoted by $z=1$. The slice at the lowermost position among the slices in the image I1 is denoted by $z=180$. In the following, a coordinate system (axis) is represented herein by a capital letter (Z), and a coordinate value in the coordinate system is represented herein by a lower-case letter (z). A coordinate system represented by Z is a coordinate system whose origin corresponds to the slice at the uppermost position among the slices in the image, with coordinate values (z) increasing on a slice-by-slice basis such that the coordinate value of each slice in the Z axis may change depending on the imaging range or the size of the body (bone) of the subject. That is, in this coordinate system, the positions of slice images indicated by z=0 in different three-dimensional images are not always at substantially the same anatomical position. In the example illustrated in FIG. 5, the top of the cervical spine, the top of the thoracic spine, the top of the lumbar spine, the top of the sacrum, and the lowest point of the ischium in the image I1 are assumed to be at positions indicated by z=0, z=23, z=96, z=140, and z=180, respectively. The process of obtaining the positions of the anatomically characteristic cross sections corresponds to an example of position obtaining means for obtaining position information indicating the position of an anatomically characteristic cross section of a subject, the anatomically characteristic cross section indicating a boundary of a segment.

The process of determining a belonging segment of each slice in the image I1 refers to an operation of assigning a specified segment to each of the slices at the positions indicated by z=0 to z=180. In the example illustrated in FIG. 5, slices in the range indicated by z=[0, 23] are ideally assigned the "segment 2". Likewise, desirably, slices in the range indicated by z=(23, 96] are assigned the "segment 3", slices in the range indicated by z=(96, 140] are assigned the "segment 4", and slices in the range indicated by z=(140, 180] are assigned the "segment 5".

The belonging segment determination process described above may be automatically performed, as desired, by utilizing matching processing based on existing image feature values on a slice-by-slice basis. This method involves creating, before performing the determination process, a database including data sets, each of which is obtained by associating information on an image feature value computed from a certain slice with information on a specified segment corresponding to the slice. The information on each of the image feature values may be information on pixel values in the corresponding slice or information on output values of various image filters applicable to the corresponding slice. In a more specific example, features of a bone appearing in a CT image may be captured by utilizing a fact that bone regions have high pixel values. Specifically, the volume of a portion having pixel values greater than or equal to a certain threshold (e.g., 150 H.U.) may be used as a feature value. Alternatively, a histogram of the pixel values included in the image may be used as a feature value.

The following describes an example of a method of, in response to input of an unknown three-dimensional image, determining a belonging segment of each slice in the image by utilizing matching in feature value to data sets included in a database. The matching may be implemented as follows. First, a degree of similarity is computed between information on a feature value computed from a certain slice in the input image and information on each of the feature values stored in advance in the database. Then, the data set having the highest degree of similarity among the computed degrees of similarity is selected from among all the data sets. Accordingly, matching between the input image and an image in the database is implemented. The belonging segment of the slice being processed can be determined by assigning information on the specified segment associated with the data set having the highest degree of similarity, which is obtained as a result of the matching, as information on the belonging segment of the slice. Similar processing is performed on all the slices included in the three-dimensional image to automatically determine segments to which the respective slices belong. In addition to the data set having the highest degree of similarity, a predetermined number of data sets from the data set having the highest degree of similarity may be selected, and segments may be assigned using results of integrating pieces of information on the belonging segments by using a method such as majority rule.

In the process of assigning information on a belonging segment described above, constraints based on the features of anatomical structures of the human body may be provided. For example, when the segment definition information illustrated in FIG. 3 is used, no other segment should be present between the segments 1 and 2 (e.g., the lumbar spine is not present between the parietal part and the thoracic spine), which is known in advance. On the basis of this knowledge, when pieces of information on belonging segments are assigned to slices in an input three-dimensional image in sequence from the slice at the uppermost (or lowermost) position, the number of data sets to be used for matching may be limited on the basis of information on a belonging segment of a slice positioned above (or below) the slice being processed. That is, removing a data set associated with information that is not suitable as an estimation result from the database can prevent inappropriate assignment. In addition, the limitation of the number of data sets for matching can reduce the time taken for computation.

While an example has been provided in which belonging segments are determined on a slice-by-slice basis by using feature values computed on a slice-by-slice basis, processing may be performed in increments of a plurality of slices of a three-dimensional image. Also in this case, information on feature values computed from a plurality of slices may be used to compute a degree of similarity between the input image and an image of each data set. Further, in the determination of belonging segments, a single slice included in the three-dimensional image (e.g., the slice at the center of the three-dimensional image) may be assigned information on a belonging segment, or each of the slices in the three-dimensional image may be assigned information on a belonging segment.

The method for determining belonging segments on a slice-by-slice basis, described above, is an example, and any other alternative means may be used to perform equivalent processing. For example, the positions of anatomically characteristic cross sections corresponding to the boundaries of the belonging segments described above may be estimated by using similar matching processing, and a corresponding segment may be assigned between a plurality of anatomically characteristic cross sections to determine a belonging segment. This process corresponds to an example of position obtaining means for obtaining position information indicating the position of an anatomically characteristic cross section, on which a boundary of an anatomical structure is delineated, in an image. This process further corresponds to an example of segment identifying means for identifying, based on the obtained position information of the anatomically characteristic cross section, a segment to which a cross section corresponding to a slice image belongs.

Finally, the segment determination unit 52 searches for slices in the images I1 to IN, which correspond to a boundary of each belonging segment, on the basis of the information on the determined belonging segments, and stores the search results in the RAM 33.

Step S104: Calculation of Coordinate Value of Each Slice in Each Image in Reference Coordinate System Corresponding to Each Belonging Segment In step S104, the coordinate calculation unit 53 calculates, based on information on the belonging segment of each slice determined in step S103, the coordinate value of the slice in the reference coordinate system corresponding to the belonging segment, and stores the coordinate value in the RAM 33. This e computation is performed on all of the images I1 to IN.

Figure 6:
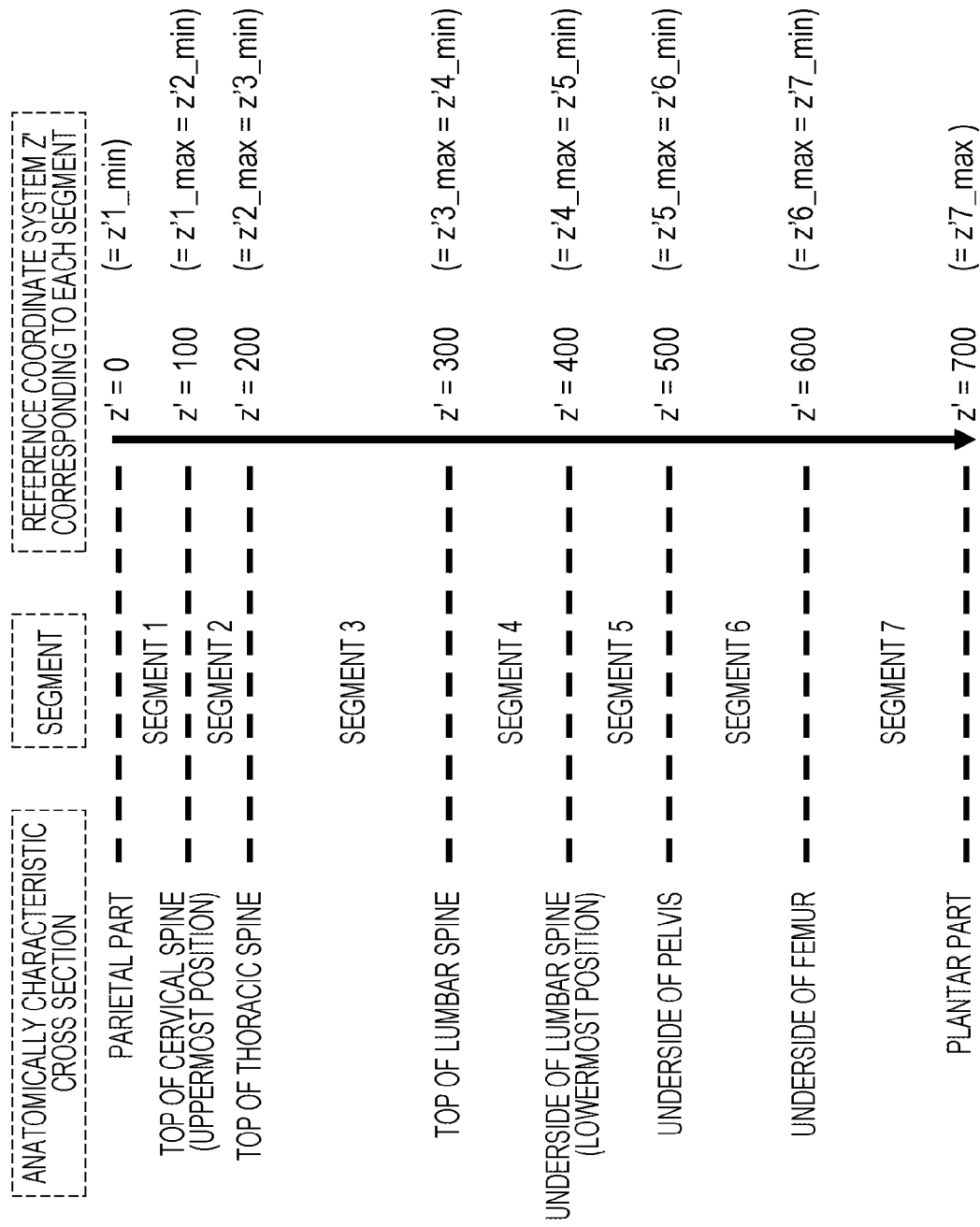
FIG. 6 illustrates an example of reference coordinate systems Z', each of which is defined for a segment.
Figure 7:
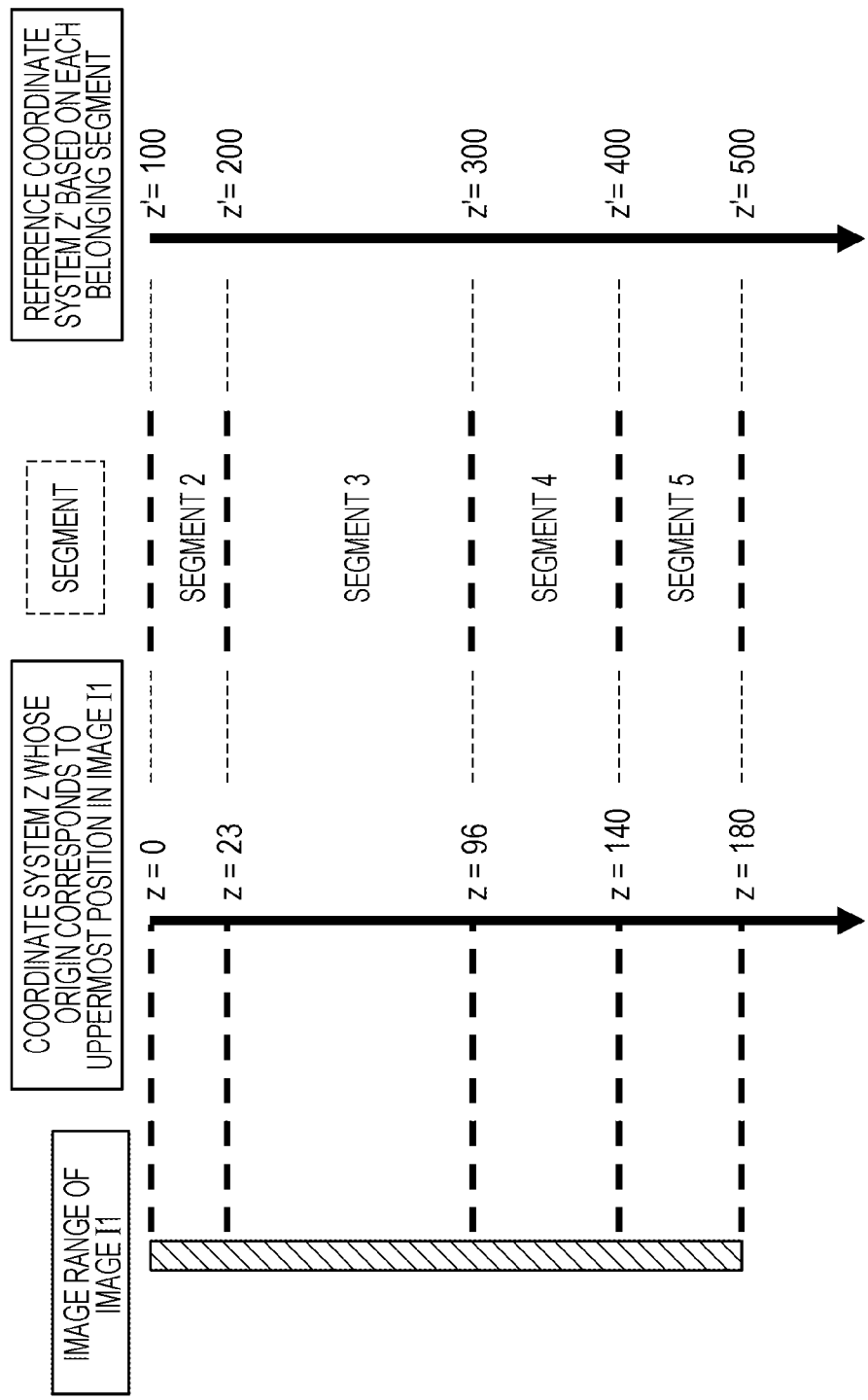
FIG. 7 illustrates an example of use of the reference coordinate systems Z' and a coordinate system z whose origin corresponds to the uppermost position in the image I1 in the example illustrated in FIG. 5.

FIG. 6 illustrates an example of reference coordinate systems Z', each of which is defined for one of the segments in the segment definition information illustrated in FIG. 3. In the illustrated example, a minimum value and a maximum value of a reference coordinate system Z' for a segment n are denoted by z'n_min and z'n_max, respectively. In the reference coordinate systems Z' illustrated in FIG. 6, the coordinate value of a slice corresponding to the parietal part is defined by z'=0, and the coordinate value of a slice corresponding to the top of the cervical spine is defined by z'=100. That is, the minimum value and the maximum value for the segment 1 are given by z'1_min=0 and z'1_max=100, respectively. The minimum value for the segment 2 is set to be equal to the maximum value of the segment 1, namely, z'2_min=z'1_max, thereby making coordinate values consecutive in the boundary of the segments 1 and 2. Also for the anatomically characteristic cross sections below the top of the cervical spine, the coordinate value increases by 100 for each characteristic cross section when it moves downward, such that the coordinate value of the lowermost slice, which corresponds to the plantar part, is indicated by z'=700. FIG. 7 illustrates an example based on the example illustrated in FIG. 5, in which the coordinate system Z whose origin corresponds to the uppermost position in the image I1 and the reference coordinate systems Z' are associated. In FIG. 7, the position indicated by z=0 corresponds to the position indicated by z'=100, and the position indicated by z=23 corresponds to the position indicated by z'=200.

The coordinate system Z and the reference coordinate systems Z' illustrated in FIG. 7 may be associated in position by the following processing. First, the coordinate calculation unit 53 associates the position of a slice corresponding to a boundary of each belonging segment with the position of the boundary of the segment in a reference coordinate system. Then, the coordinate calculation unit 53 associates positions of non-boundary portions. In the illustrated example, anatomical structures included in the same belonging segment in the coordinate system Z and the reference coordinate systems Z' are regarded as being arranged with substantially the same balance of sizes thereof although the scales are different. Accordingly, the coordinate calculation unit 53 linearly associates coordinates in the coordinate system Z and the reference coordinate systems Z' for each belonging segment. Specifically, slices in the range of coordinates z=[0, 23], which corresponds to the segment 2, are regarded as having coordinate values that increase linearly, and the coordinate values in the reference coordinate system Z' therefor are computed using the equation below, for example. In the equation, f(z) denotes a coordinate value in the reference coordinate system Z' that corresponds to a coordinate value z of a slice.

$$f(z)=z'n\_min+(z-zn\_min)/(zn\_max-zn\_min)\times(z'n\_max-z'n\_min) \quad \text{Eq. (1)}$$

In Eq. (1), zn_min is a minimum value of the coordinate values z of the slices in the segment n, and zn_max is a maximum value of the coordinate values z of the slices. In a specific example, f(z) is computed, assuming that the position indicated by z=10 in FIG. 7 is assigned "the segment 2". In this case, the respective parameters are z2_min=0, z2_max=23, z'2_min=100, and z'2_max=200. For the other belonging segments, the minimum value and maximum value of slices in each of the belonging segments are substituted into the respective parameters in a similar way. Accordingly, a coordinate value in a normalized coordinate system can be computed for each belonging segment by using Eq. (1). The method for associating positions of non-boundary portions is not limited to the method described above, and the positions of non-boundary portions may be associated nonlinearly.

The effect of providing the reference coordinate system Z' will be described. The effect of setting the reference coordinate system Z' is that for anatomically characteristic cross sections in different three-dimensional images that are defined in segment definition information, substantially the same anatomical locations have the same coordinate value in the reference coordinate system Z'. Using information on the normalized space advantageously facilitates subsequent processing of aligning and displaying different three-dimensional images.

To enhance spatial normalization, segment definition information is defined such that anatomical structures of the human body can be separated into finer segments. Accordingly, normalization can be implemented in finer units. For example, segment definition information includes only two anatomically characteristic cross sections of the parietal part and the plantar part. In this case, a space for images to be aligned is normalized such that the parietal part is assigned a minimum value and the plantar part is assigned a maximum value in the reference coordinate system Z'. The effect of normalization between these anatomically characteristic cross sections becomes weak away from the anatomically characteristic cross sections. This is because the sizes of anatomical structures of the human body differ from person to person, and different persons have different balances of sizes of anatomical structures between the anatomically characteristic cross sections (the parietal part and the plantar part). That is, if images to be aligned have different balances of sizes of anatomical structures included in the images, even slices given the same coordinate value in the reference coordinate system may not be located at anatomically corresponding positions. The different balances may be caused generally by age difference or the like, and may also be somewhat caused due to variations in individuals. An increase in the number of anatomically characteristic cross sections included in the segment definition information corresponds to separating anatomical structures of the human body into a plurality of segments at anatomically meaningful positions along the body axis and normalizing an image in a reference coordinate system (normalized space) provided for each segment. Normalization using sub-spaces may result in different balances of sizes of anatomical structures being absorbed in smaller units, which is effective for normalization.

Step S105: Display of Image Based on Coordinate Value in Reference Coordinate System In step S105, the alignment unit 54 determines slices having the same or substantially the same coordinate value in the reference coordinate system ZT for the images I1 to IN on the basis of the coordinate value calculated in step S104. Then, the display processing unit 55 displays images of the determined slices in the image display area 400 of the display unit 36. That is, the display processing unit 55 corresponds to an example of display control means for causing display means to display associated slice images in such a manner as to make the associated slice images comparable with each other. Corresponding slice images may be displayed using any known method such as side-by-side, superimposed, or time-division representation.

For example, the user operates the image I1 in an image display area of the display unit 36. In response to an instruction given from the user to display a certain slice in the image I1 (this slice is hereinafter referred to as a slice of interest), the alignment unit 54 obtains the coordinate value (ZI1') of the slice of interest in the reference coordinate system Z' from the result of computation in step S104. Then, the alignment unit 54 refers to the coordinate values of slices in each of the images I2 to IN in the reference coordinate system Z' and determines slices having closest coordinate values to the coordinate value ZI1' for the images I2 to IN as the corresponding slices of the slice of interest. Thereafter, the display processing unit 55 displays the determined slices in the image display area of the display unit 36. This processing can present to the user a certain slice of interest in the image I1, which is displayed in accordance with the user's operation, and slices (i.e., corresponding slices) including substantially the same anatomical structure as that of the slice of interest in the images I2 to IN.

The process of displaying a slice at a corresponding position, described above, does not need to be performed for each of the images I1 to IN, and may be performed only for an image selected by the user through the operation unit 35.

In addition, as described above, a slice image indicating a cross section between anatomically characteristic cross sections has an effect of normalization that becomes weak as the distance from the anatomically characteristic cross sections increases. Accordingly, the display processing unit 55 may change the display style of the slice image in accordance with the distances between the cross section indicated by the slice image to be displayed and the anatomically characteristic cross sections. For example, the display processing unit 55 sets the color of the edge of the slice image to red when the distance between the cross section indicated by the slice image to be displayed and the closest anatomically characteristic cross section is larger than a predetermined distance. When the distance between the cross section indicated by the slice image to be displayed and the closest anatomically characteristic cross section is not larger than the predetermined distance, the display processing unit 55 sets the color of the edge of the slice image to blue. Accordingly, by changing the display style of a slice image depending on whether the distance between the cross section indicated by the slice image to be displayed and the closest anatomically characteristic cross section is larger than a predetermined distance, the user is able to determine the reliability of the normalization described above. The display style may be changed not only in color but also in character or symbol. Alternatively, information on the distance from the closest anatomically characteristic cross section may be displayed directly without performing threshold processing using a predetermined distance. In this case, the distance may be the number of slices, the physical distance (in mm), or a distance in the reference coordinate system Z'. Alternatively, a pseudo color assigned in accordance with the distance may be set as the color of the edge of a slice image.

According to this embodiment, different balances of sizes of anatomical structures of the human body can be absorbed by normalizing the positions of the anatomical structures for each site along the body axis. Accordingly, advantageously, it is possible to provide more accurate alignment results to the user in a process of aligning different images.

First Modification

The embodiment described above provides an example in which during a user's observation (diagnosis) using a plurality of three-dimensional images that are displayed, the coordinate value of each slice in each image in the reference coordinate system Z' is computed. However, the procedure for performing the process of computing a reference coordinate value of each slice is not limited to that described above. For example, the image processing apparatus 10 may perform the processing of steps S101 to S104 to compute the coordinate value of each slice in each of the images I1 to IN in the reference coordinate system Z'. The result of the computation may be attached to each image as auxiliary information of the slice and stored in the database 22. In this case, in the processing of step S102, no image may be displayed. Additionally, a plurality of images to be compared need not be processed simultaneously, but may be processed separately. In this case, this process can be executed, prior to the doctor's observation (diagnosis) using images, at a timing such as immediately after each image is captured. That is, this procedure corresponds to the execution of the processing of steps S103 to S104 on each image in advance.

At the time of the user's observation (diagnosis) using images, the image processing apparatus 10 can perform the processing of steps S102 and S105. In this procedure, when the image obtaining unit 51 obtains an image in step S102, the process of reading a reference coordinate value of each slice, which is stored as auxiliary information of the image, is added. Accordingly, processing equivalent to that in the first embodiment can be implemented.

The process according to the first modification can remove the computation of a coordinate value in the reference coordinate system 2' when displaying an image, which is performed in the first embodiment. The waiting time of the user during observation (diagnosis) using images can be shortened.

It may be determined whether an obtained image has a reference coordinate value of each slice as auxiliary information, and the processing of steps S103 and S104 may be executed on the image only when the image does not have the auxiliary information. This can minimize the waiting time for calculation of a reference coordinate value when both a processed image and an unprocessed image exist.

Second Modification

In the first embodiment, in step S105, the alignment unit 54 performs computation to determine a corresponding slice of a certain slice of interest in a three-dimensional image in response to the user designating the slice of interest as a trigger. However, this procedure is not limited to this method. For example, in the processing of step S105, the alignment unit 54 may determine the correspondence between slices in all of the images I1 to IN in advance by using the reference coordinate system Z'. This configuration allows each slice in each image to have identifiers (slice numbers) of corresponding slices in other images as auxiliary information. When the user designates a slice of interest, the display processing unit 55 may read the identifiers of the corresponding slices, which are included in the slice of interest, and display the image of the slice of interest and the images of the corresponding slices together. This can remove the computation to determine a corresponding slice when displaying an image, which is performed in the first embodiment and the first modification. Accordingly, in response to an instruction given from the user to display a slice in a certain image, corresponding slices in other images can be displayed immediately.

Other Embodiments

Embodiments of the present invention may also be implemented as follows. A program implementing one or more functions in the embodiment described above is provided to a system or an apparatus via a network or a storage medium, and one or more processors in a computer of the system or apparatus read and execute the program. The embodiments of the present invention may also be implemented by a circuit that implements one or more functions (e.g., an application-specific integrated circuit (ASIC)).

Second Embodiment

In the first embodiment, in step S103, the segment determination unit 52 determines to which of a plurality of segments included in segment definition information each of slices constituting the images I1 to IN belongs. Then, in step S104, the coordinate calculation unit 53 searches for the position of the boundary of each belonging segment and associates the found position with the position of the boundary in a reference coordinate system corresponding to the segment definition information to implement spatial normalization. However, any other method may be used to implement the spatial normalization described above.

A second embodiment provides an example of a method to be performed on a three-dimensional image obtained by the image obtaining unit 51 to directly estimate positions of an anatomically characteristic cross sections included in the segment definition information and to perform spatial normalization using results of the acquisition of the positions of the cross sections. This embodiment advantageously makes it possible to perform a process based on information on an entire three-dimensional image, and can provide more accurate association than slice-by-slice matching described in the first embodiment.

An image processing apparatus according to the second embodiment has the same configuration as that in the first embodiment, except that the segment determination unit 52 additionally has the following function.

In the second embodiment, the segment determination unit 52 performs cross-section position estimation processing on each of the images I1 to IN to be aligned, to obtain positions of anatomically characteristic cross sections included in segment definition information from within a range of the image.

A second example of the process flow of the image processing apparatus 10 will be described with reference to FIG. 8.

Figure 8:
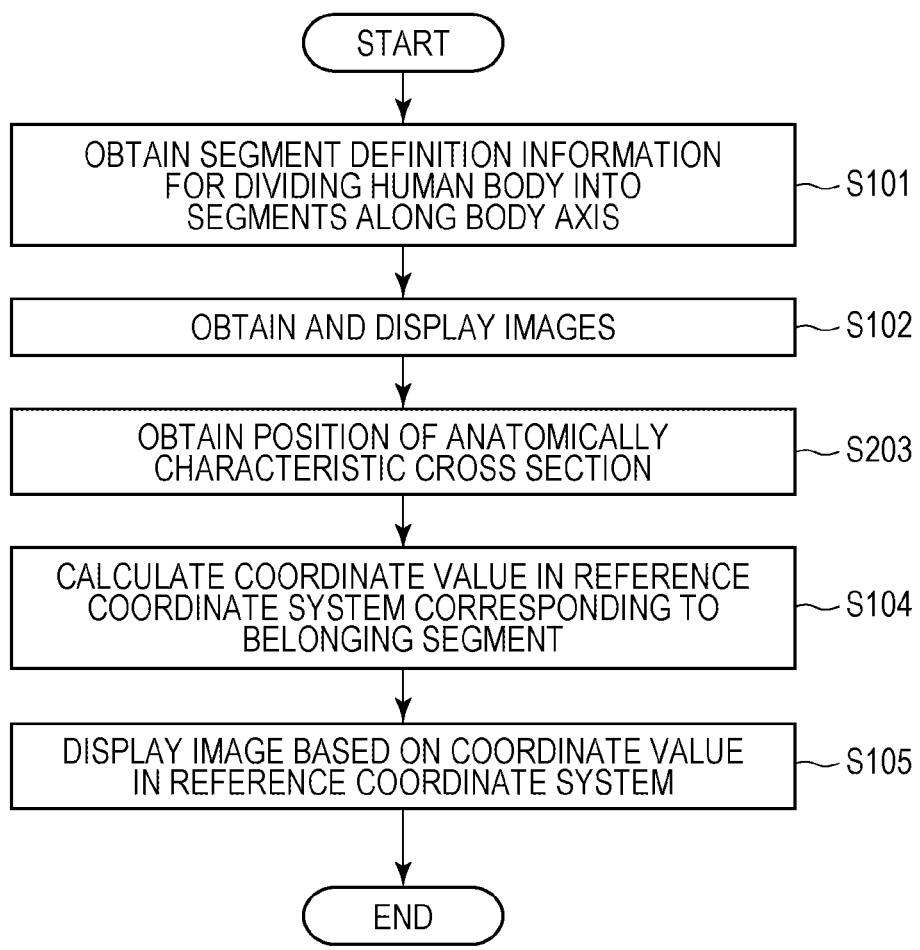
FIG. 8 is a flowchart illustrating a second example of the operation procedure of the image processing apparatus.

FIG. 8 is a flowchart illustrating an example process for displaying a plurality of images that are aligned in position in a certain reference coordinate system. The illustrated process starts from a process of obtaining segment definition information, which is performed by the image processing apparatus 10. Among the steps in the illustrated flowchart, steps S101 to S102 and S104 to S105 are similar to steps S101 to S102 and S104 to S105 according to the first embodiment illustrated in FIG. 2. That is, the difference from the process according to the first embodiment is step S203. The following describes only the difference between the added process and the process according to the first embodiment.

Step S203: Obtaining of Position of Anatomically Characteristic Cross Section

In step S203, the segment determination unit 52 estimates positions of anatomically characteristic cross sections included in the segment definition information from within the three-dimensional images (the images I1 to IN) obtained by the image obtaining unit 51, and stores the estimated positions in the RAM 33.

The process described above may be implemented by using an existing alignment technique for the three-dimensional images. Also when positions of anatomically characteristic cross sections are estimated using the alignment technique, a certain database is created, as in the first embodiment. In the second embodiment, as a data set, data that associates a three-dimensional image (reference image) with position information of a specified anatomically characteristic cross section is used. When estimating positions of anatomically characteristic cross sections from within an image by performing an alignment process, it is desirable that the reference image in the database have a wider range than an input three-dimensional image. This is because if the image in the database has a smaller range than an input three-dimensional image, estimation of positions of anatomically characteristic cross sections may fail since a cross section corresponding to an anatomically characteristic cross section included in the input three-dimensional image may not be contained in the image.

In a method using the alignment technique described above, the segment determination unit 52 performs three-dimensional image alignment between each of images of input three-dimensional image data (the images I1 to IN) and an image (reference image) of a data set included in the database. That is, this process corresponds to an example of alignment means for aligning an obtained image with a three-dimensional reference image including slice images, each of which is associated with information on a segment. Here, it is sufficient that alignment be performed in position between each of the images I1 to IN and a reference image only along an axis along which anatomically characteristic cross sections are defined. The alignment in position along a single axis can be implemented by, for example, performing optimization processing to maximize a degree of similarity between images to be aligned with respect to the processing target axis. The degree of similarity between images may be obtained using the sum or squared sum of the absolute values of the density values or feature values of the images, or using any other index.

The position of an anatomically characteristic cross section in the image I1 may be estimated using the database in the following way. First, the segment determination unit 52 performs the alignment process described above on the image I1 and the images of all the data sets. Through the alignment process, a shift and a degree of similarity between the image I1 and each of the images of the data sets can be computed. A shift ($\Delta z$) between images represents a difference between coordinate values zTest and zRef, where the coordinate values zTest and zRef of represent coordinate values at corresponding cross section positions in an input image and an image of a data set, respectively. That is, $\Delta z = z\text{Test} - z\text{Ref}$. The coordinate values zTest and zRef are coordinate values obtained when the positions of the uppermost slices of the respective images are assumed to be the origins.

Then, the segment determination unit 52 selects the data set that is the most similar to the input image among all the data sets on the basis of the maximum value of the degrees of similarity between the images that are computed for all the data sets.

Finally, the segment determination unit 52 estimates position information of an anatomically characteristic cross section in the input image on the basis of position information of a specified anatomically characteristic cross section associated with the image of the selected data set (reference image). That is, this process corresponds to an example of segment identifying means for estimating a segment to which a cross section corresponding to a slice image included in an image belongs, based on information on a segment associated with a slice image included in an aligned reference image.

In the process of estimating position information of an anatomically characteristic cross section, since a shift ($\Delta z$) between an input image and the selected reference image is computed through the previous processing, this information is used. Specifically, the sum and the shift ($\Delta z$) of position information of a specified anatomically characteristic cross section associated with the selected reference image is computed to estimate the position of the anatomically characteristic cross section in the input image.

While an example has been described in which only data with the highest degree of similarity is used, any other estimation method may be used. For example, a plurality of pieces of data, the number of which is determined in advance, may be selected in order from the highest degree of similarity, and the average or any other suitable value of the plurality of pieces of data may be used to estimate a position.

A slice located between a plurality of anatomically characteristic cross sections included in the input image may be assigned a belonging segment defined in the segment definition information. As in this embodiment, if the positions of anatomically characteristic cross sections can be estimated, the process of estimating a belonging segment using each slice, which is described in the first embodiment, may be omitted. This is because the computation of step S104 by the coordinate calculation unit 53 may be carried out if a position information of an anatomically characteristic cross section included in the input image and a reference coordinate system corresponding to each segment included in the segment definition information are defined.

This embodiment makes it possible to perform a process based on information on an entire three-dimensional image, and can provide more accurate association than slice-by-slice matching described in the first embodiment.

Third Embodiment

In the second embodiment, in step S203, the segment determination unit 52 aligns each of the three-dimensional images (the images I1 to IN) obtained by the image obtaining unit 51 with the image included in the database to estimate positions of anatomically characteristic cross sections. Then in step S104, the segment determination unit 52 computes, based on the estimated positions of the anatomically characteristic cross sections, coordinate values in the reference coordinate system Z'.

An image processing apparatus according to a third embodiment has the same configuration as that in the second embodiment, except that the segment determination unit 52 additionally has the following function.

In the third embodiment, the segment determination unit 52 performs cross-section position estimation processing on each of the images I1 to IN to be aligned, to obtain positions of anatomically characteristic cross sections included in segment definition information from within a range of the image. The fundamental function in the third embodiment is similar to that in the second embodiment, and the difference from the second embodiment is as follows. The third embodiment provides an additional function of estimating not only a position of an anatomically characteristic cross section within a range of an input image but also a position of an anatomically characteristic cross section outside the range and computing coordinate values in the reference coordinate system Z' on the basis of the estimation results. This function corresponds to an example of position obtaining means for estimating a position of an anatomically characteristic cross section of a subject outside an imaging range, which is included in an image, obtain position information indicating the position of the anatomically characteristic cross section outside the imaging range. Accordingly, it is possible to estimate the position of an anatomically characteristic cross section outside an image range for a site that is partially visible due to the upper and lower ends of an image along the body axis. That is, even when a slice is not located between anatomically characteristic cross sections within the range of an image, a coordinate of the slice can be associated with a coordinate in a more accurate reference coordinate system. The following describes the additional process and the difference from the second embodiment.

The method according to the first embodiment and the second embodiment allows computation of a coordinate value of a slice located between a plurality of estimated anatomically characteristic cross sections in the reference coordinate system Z'. As in an image A1 illustrated in FIG. 9, when the positions of the plurality of anatomically characteristic cross sections correspond to the positions of ends of an input image (the image A1), coordinate values of all the slices constituting the image A1 in the reference coordinate system Z' can be computed. However, when the input image has a range such as the range of an image A2, an image A3, and an image A4 illustrated in FIG. 9, it is difficult to compute coordinate values of some or all of the slices constituting the input image in the reference coordinate system Z'. This because if only a plurality of anatomically characteristic cross sections included in the range of the image are used in this situation, some or all of the slices constituting the image A2, the image A3, and the image A4 may not be located between the anatomically characteristic cross sections. That is, the parameter zn_max and/or zn_min, which is used for the computation (Eq. (1)) of step S104 by the coordinate calculation unit 53, is difficult to obtain, and it is difficult to compute coordinate values of such slices in the reference coordinate system Z'.

To address the difficulties, in step S203, the segment determination unit 52 according to this embodiment estimates a position of an anatomically characteristic cross section within the range of an input image in a way similar to that in the second embodiment, and further estimates a position of an anatomically characteristic cross section outside the range of the image. Also, the coordinate calculation unit 53 estimates a position of an anatomically characteristic cross section outside the range of the input image by using the computation method described in the second embodiment in step S104. Accordingly, the coordinate calculation unit 53 can compute a coordinate value of each of the slices constituting the input image in the reference coordinate system. When a cross section included in the input image corresponds to a cross section of an edge in the segment definition information (in FIG. 3, the parietal part or the plantar part), there is no need to estimate a cross section outside the cross section.

A position of an anatomically characteristic cross section outside the range of the input image may be estimated by using a method similar to that based on the alignment technique described in the second embodiment. Note that when a position of an anatomically characteristic cross section in an input image is computed using a position of an anatomically characteristic cross section associated with an image of a data set, it is necessary to expand the range of the computation. That is, it is necessary to compute not only a position of an anatomically characteristic cross section within the imaging range in the input image but also a position of an anatomically characteristic cross section indicated by a coordinate outside the imaging range in the input image. To implement the computation of the position of the cross section, a constraint needs to be provided such that when a data set is selected from the database, only a data set satisfying a certain condition is used for processing.

The condition is that after alignment with the input image, the input image and an image of a data set are common in part, and an anatomically characteristic cross section outside the range of the input image is associated with the data set.

The following two patterns of data sets may satisfy the condition. The first pattern is that a plurality of anatomically characteristic cross sections associated with the data set include the range of the input image (or are located so as to sandwich the range of the input image therebetween) (pattern 1). The second pattern is that either the upper or lower cross section among anatomically characteristic cross sections outside the range of the input image is associated with the data set (pattern 2).

The following provides an example of estimation methods using the two patterns of data sets as an example of a specific process flow of a method of estimating a position of an anatomically characteristic cross section outside the range of an input image.

Estimation Method Using Data Set (Group) of Pattern 1

First, the processing up to alignment in position between an input image and the image in the database is performed in a way similar to that in the process flow described in the second embodiment. After the alignment process, a data set indicating a maximum value of the degrees of similarity between the images is selected from among the data sets that matches the pattern 1. Finally, positions of cross sections in the input image in the coordinate system Z, including anatomically characteristic cross sections outside the range of the input image, are estimated for the positions of all the anatomically characteristic cross sections associated with the image of the selected data set. The selection of a data set is not limited to selection of a data set indicating the maximum value of the degrees of similarity, and a predetermined number of data sets may be selected in order from the highest degree of similarity. In the selection of a plurality of data sets, a position of a cross section in the input image in the coordinate system Z may be estimated for an anatomically characteristic cross section associated with each of the data sets, by computing the mean (or maximum, minimum, or the like) of the coordinate values of the same cross section.

Figure 9:
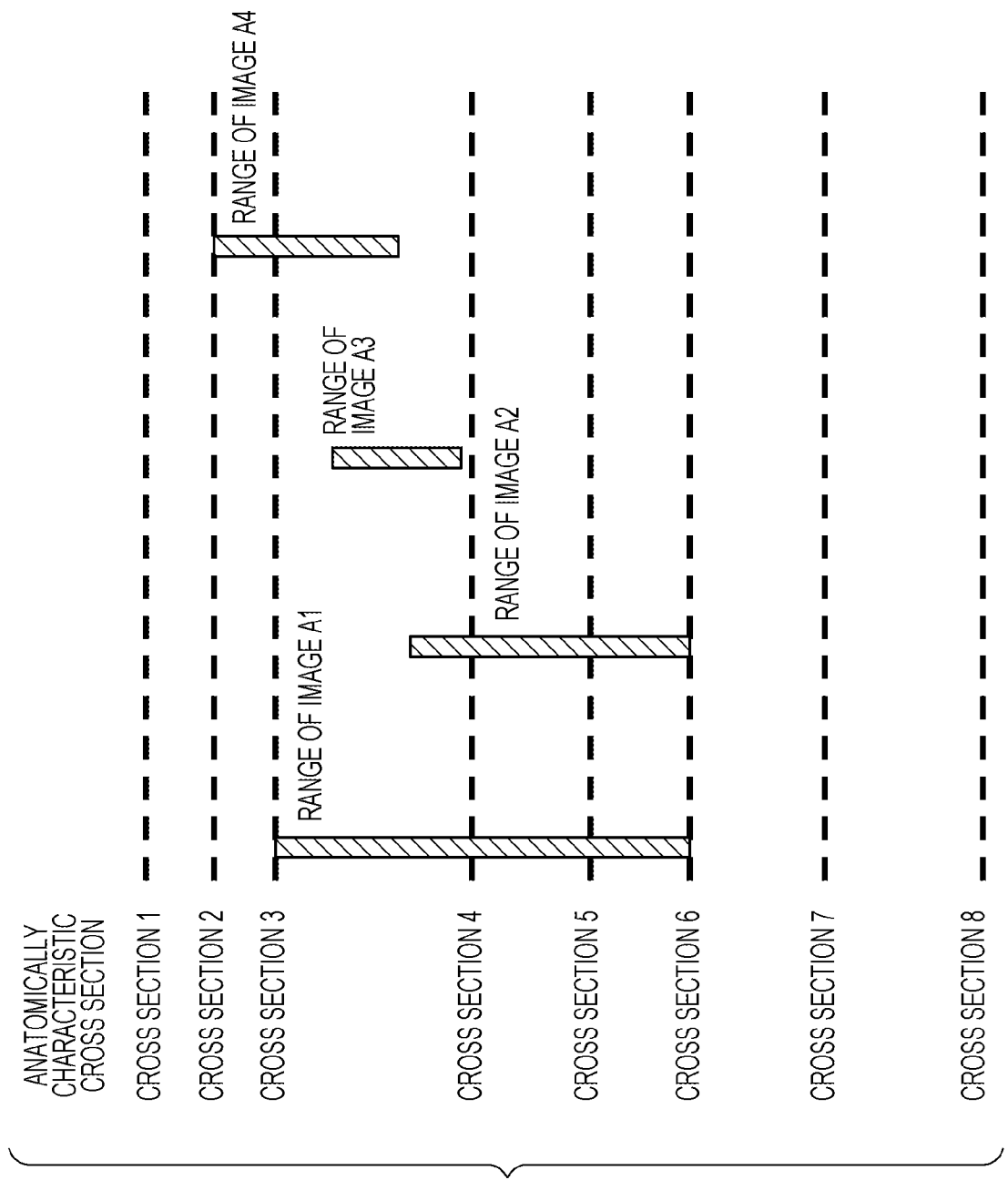
FIG. 9 illustrates an example of relationships between ranges of certain images and results of estimating positions of anatomically characteristic cross sections.

Whether a certain data set matches the pattern 1 may be determined in the following way. First, the cross section at the uppermost position and the cross section at the lowermost position are determined in position among a plurality of anatomically characteristic cross sections included in the data set. Then, whether the range of the input image is between the determined cross sections can be checked to determine whether the data set matches the pattern 1. In a specific example, the image A3 illustrated in FIG. 9 is input data, and the image A1 and the image A2 are images of data sets included in the database. It is assumed here that, in FIG. 9, the alignment of the images A1, A2, and A3 has been completed.

First, consideration is given of the input image A3 and the image A1 included in the database. The anatomically characteristic cross sections included in the image A1 are cross sections 3, 4, 5, and 6. Among the cross sections 3 to 6, the cross section 3 is at the uppermost position, and the cross section 6 is at the lowermost position. The range of the image A3 is checked. The range of the image A3 is found to be between the cross sections 3 and 6. That is, it can be determined that the image A1 included in the database satisfies a condition for estimating the positions of the anatomically characteristic cross sections outside the range of the input image A3 and matches the pattern 1.

Then, consideration is given of the input image A3 and the image A2 included in the database. The anatomically characteristic cross sections included in the image A2 are the cross sections 4, 5, and 6. Among the cross sections 4, 5, and 6, the cross section 4 is at the uppermost position, and the cross section 6 is at the lowermost position. The range of the image A3 is checked in a way similar to that described above. A portion of the range of the image A3 is found not to be between the cross sections 4 and 6. That is, it can be determined that the image A2 included in the database satisfies a condition for estimating the positions of the anatomically characteristic cross sections outside the range of the input image A3, but does not match the pattern 1 (i.e., the image A2 matches the pattern 2).

Figure 10:
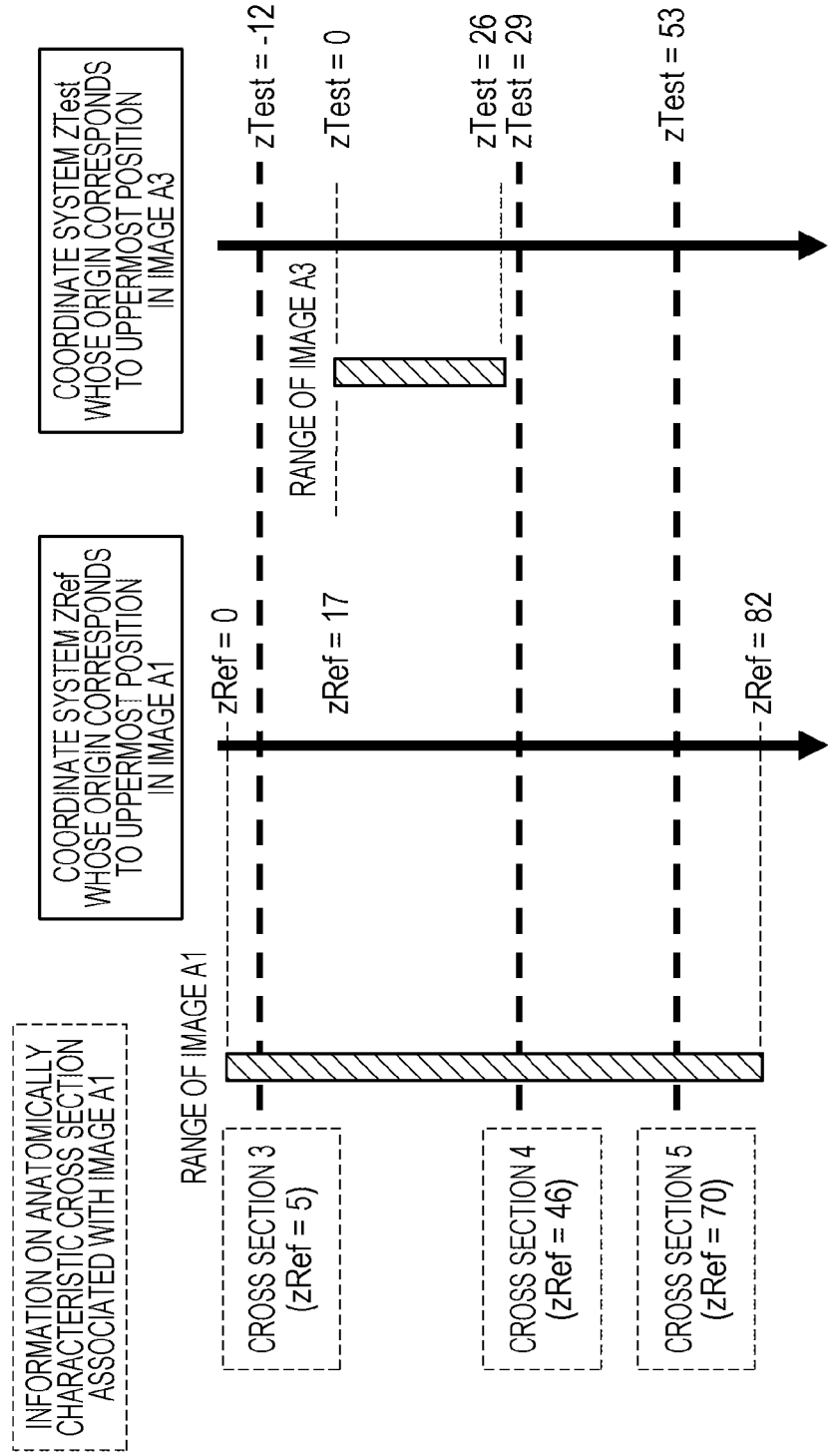
FIG. 10 illustrates an example of a relationship between a result of estimating a position of an anatomically characteristic cross section outside a range of an input image and a coordinate value in a coordinate system whose origin corresponds to the uppermost position (slice) in the input image.

Finally, a method of estimating a position of a cross section in the input image in the coordinate system Z, including anatomically characteristic cross sections outside the range of the input image, on the basis of positions of anatomically characteristic cross sections associated with an image in the database will further be described with reference to FIG. 10. In an example illustrated in FIG. 10, the image A3 is an input data, and the image A1 is an image in the database. It is assumed that the alignment of the images A1 and A3 has been completed. In FIG. 10, a coordinate system ZRef whose origin corresponds to the uppermost position in the image A1 and a coordinate system ZTest whose origin corresponds to the uppermost position in the image A3 are defined. Now, as a result of the alignment of the image A1 and the image A3, a shift $\Delta z$ (=zTest−zRef) for calculating corresponding positions in these coordinate systems −17. In addition, the image A1 in the database has the positions indicated by zRef=5, 46, and 70 that are associated with information on the characteristic cross sections, namely, the cross sections 3, 4, and 5, respectively. Assuming that the position of the cross section 3 (zRef=5) in the coordinate system ZTest is given by zTest=zRef$\Delta z$. That is, zTest=5 (−17)=−12. The same computation can be applied to the cross section 4, and the position of the cross section 4 is given by zTest=29. Since the range of the image A3 is represented by zTest=[0, 26], it is found that the positions of the anatomically characteristic cross sections outside the range of the image A3 are successfully estimated.

The estimation method described above is an example, and any other method may be used to estimate positions of anatomically characteristic cross sections outside the range of the image. For example, another method of estimating a position of an anatomically characteristic cross section outside the range of an input image may be to, as described below, perform estimation processing by using two or more data sets in the database in combination.

Estimation Method Using Data Set Group of Pattern 2

In the estimation method using a data set satisfying the pattern 1, an example is illustrated in which data sets having both upper and lower cross sections are utilized for anatomically characteristic cross sections outside the range of an input image. However, when two or more data sets are used in combination, a database including a plurality of data sets that match the pattern 2 can be used to estimate positions of anatomically characteristic cross sections outside the range of the input image.

Also in the estimation method using a data set group that matches the pattern 2, the processing up to alignment in position between an input image and the image in the database is performed in a way similar to that in the process flow described in the second embodiment. The difference is that after the alignment process, a plurality of data sets are selected from within a data set group that matches the pattern 2 on the basis of the degrees of similarity between the images. In the estimation using a data set group of the pattern 2, a plurality of data sets are selected such that at least one data set for anatomically characteristic cross sections outside the range of the input image is included for each of the upper and lower sides of the range of the input image. Finally, positions of cross sections in the input image in the coordinate system Z, including anatomically characteristic cross sections outside the range of the input image, are estimated on the basis of the positions of all the anatomically characteristic cross sections associated with the images of the selected plurality of data sets.

In the computation of positions of anatomically characteristic cross sections outside the range of the input image, a plurality of data sets may be used for the computation of each of the upper side and the lower side. Specifically, in estimation processing using anatomically characteristic cross sections associated with a plurality of data sets, a position of a cross section in the input image in the coordinate system Z may be estimated from the plurality of data sets, by computing the mean (or maximum, minimum, or the like) of the coordinate values of the same cross section between the data sets.

In a specific example, the image A3 illustrated in FIG. 9 is input data, and the image A2 and the image A4 are images of data sets included in the database. It is assumed here that, in FIG. 9, the alignment of the images A2, A3, and A4 has been completed.

Consideration is given of the input image A3 and the image A2. The anatomically characteristic cross sections included in the image A2 are the cross sections 4, 5, and 6. The range of the image A3 is checked. The cross section 4 is found to be outside the range of the image A3 and to be an anatomically characteristic cross section on the lower side. Likewise, consideration is given of the input image A3 and the image A4. The anatomically characteristic cross sections included in the image A4 are the cross sections 2 and 3. The cross section 3 is found to be outside the range of the image A3 and to be an anatomically characteristic cross section on the upper side. That is, the image A2 and the image A4 satisfy a condition for estimating the positions of the anatomically characteristic cross sections outside the range of the image A3 and match the pattern 2. As described above, through estimation processing using these data sets (the image A2 and the image A4) in combination, both the upper and lower cross section positions can be estimated for the anatomically characteristic cross sections outside the range of the input image. That is, information on the anatomically characteristic cross sections of the image A4 (the cross sections 3 and 2) can be used for the upper side outside the range of the image A3, thereby estimating the positions of the anatomically characteristic cross sections. Further, information on the anatomically characteristic cross sections of the image A2 (the cross sections 4, 5, and 6) can be used for the lower side outside the range of the image A3, thereby estimating the positions of the anatomically characteristic cross sections.

Through the process described above, it is possible to obtain information on anatomically characteristic cross sections outside the range of an input image, which are used to compute coordinate values in the reference coordinate system ZT.

Even when a position of an anatomically characteristic cross section outside the range of an image is obtained using the estimation method described above, the coordinate calculation unit 53 can compute a coordinate value in the reference coordinate system Z' in step S104 by using the method described in the second embodiment. Accordingly, the method according to this embodiment allows computation of coordinate values of all slices constituting an input image in the reference coordinate system Z'.

According to this embodiment, it is possible to estimate the position of an anatomically characteristic cross section outside an image range for a site that is partially visible due to the upper and lower ends of an image along the body axis. That is, even when a slice is not located between anatomically characteristic cross sections within the range of an image, a coordinate of the slice can be associated with a coordinate in a more accurate reference coordinate system.

Fourth Embodiment

The method of associating slices in a plurality of three-dimensional images, described in the first embodiment, is a method of computing a coordinate value in a reference coordinate system on a slice-by-slice basis in each image and associating slices in the images with each other. In this method, a single coordinate value can be computed for each slice, which causes an issue in that it is difficult to appropriately associate slices with each other when a single slice needs to be assigned a plurality of coordinates. Specific examples of this issue include anatomical structures having a slipping relationship, such as the bone and the lung. First, it is assumed that anatomically characteristic cross sections in segment definition information include the upper and lower ends of the lung. In the technique described in the first embodiment, such cross sections (slices) providing anatomical information may be assigned substantially the same coordinate value in a reference coordinate system even if the cross sections (slices) are in different three-dimensional images. However, when the lower end of the lung moves up and down, vertebral bodies do not completely follow the movement of the lung (i.e., a slip occurs), which may cause variations in the relative position of the slice of the lower end of the lung relative to the position of a certain vertebral body depending on the respiration rate of the patient at the imaging time. Accordingly, slices assigned the same coordinate value in a space normalized at the upper and lower ends of the lung may be at substantially the same anatomical position in terms of the anatomical structure of the lung, but may be at different positions in terms of the bone. That is, for example, if anatomically characteristic cross sections in the segment definition information are based on only anatomical information concerning the lung although the user is observing the bone, slices in different images are likely to be inappropriately associated with each other.

A fourth embodiment describes an example of a method of creating in advance a plurality of pieces of segment definition information, each corresponding to a different site, and selectively using a piece of segment definition information suitable for the site being observed by the user to perform spatial normalization and associate slices with each other. In this embodiment, a plurality of corresponding slices are computed for each slice, and the corresponding slices are switched in accordance with the site being observed by the user. Thus, advantageously, more sophisticated association can be provided.

An image processing apparatus according to the fourth embodiment has the same configuration as that in the first embodiment, except that the segment definition information obtaining unit 50 and the alignment unit 54 additionally have the following function.

In the fourth embodiment, the segment definition information obtaining unit 50 reads a plurality of pieces of predefined segment definition information. Further, the alignment unit 54 has a function of selectively switching corresponding slices depending on the site being observed by the user. The plurality of pieces of segment definition information are desirably information based on anatomical structures having a slipping relationship, such as the bone and the lung. The following example is described using segment definition information based on an anatomical structure related to the bone (segment definition information related to the bone) and segment definition information based on an anatomical structure related to the lung (segment definition information related to the lung), by way of example.

The operation procedure of the image processing apparatus 10 according to the fourth embodiment is similar to the operation procedure of the image processing apparatus 10 according to the first embodiment illustrated in FIG. 2. Note that processing for a plurality of pieces of segment definition information is added or changed in each step. The following describes only the additional process and the difference from the first embodiment.

Step S101

In step S101, in response to an instruction given from the user through the operation unit 35 to start image processing, the segment definition information obtaining unit 50 obtains two or more pieces of predefined segment definition information from the database 22 and stores the pieces of segment definition information in the RAM 33. For example, in an example provided in this embodiment, segment definition information related to the bone and segment definition information related to the lung are obtained. That is, a plurality of pieces of segment definition information that are based on different anatomical structures are obtained.

Then, in steps S102 to S104, processing similar to that in the first embodiment is performed. Note that the processing of steps S103 and S104 is performed on each of the plurality of pieces of segment definition information obtained in step S101.

Step S103

In step S103, the segment determination unit 52 determines a belonging segment based on each piece of segment definition information for each slice in each image. For example, in the example provided in this embodiment, a belonging segment related to the bone is determined on the basis of the segment definition information related to the bone, and a belonging segment related to the lung is further determined on the basis of the segment definition information related to the lung. This process is the same as that in the first embodiment, except that a plurality of pieces of segment definition information are used.

Step S104

In step S104, the coordinate calculation unit 53 computes coordinate values of each slice in respective reference coordinate systems $Z'$ on the basis of information on the plurality of belonging segments of the slice, which are determined in step S103. For example, in the example provided in this embodiment, a coordinate in a reference coordinate system $Z1'$ focusing on the bone and a coordinate in a reference coordinate system $Z2'$ focusing on the lung are calculated for each slice in each image. This process is the same as that in the first embodiment, except that a plurality of pieces of segment definition information are used.

Step S105

In step S105, the alignment unit 54 determines, for a slice of interest in a certain image, a corresponding slice in any other image defined for each site of interest (a corresponding slice for each site of interest). For example, the alignment unit 54 determines, for each slice of interest, a corresponding slice focusing on the lung and a corresponding slice focusing on the bone. This process corresponds to an example of association means for associating, for each of a plurality of pieces of segment definition information, slice images indicating substantially the same position in a plurality of images. Then, the display processing unit 55 selectively switches corresponding slices to be displayed, when performing a process of displaying a corresponding slice, on the basis of information on a site being observed by the user. Specifically, in response to information indicating that the user is observing the lung, the display processing unit 55 displays the slice of interest and a corresponding slice focusing on the lung in such a manner as to make the slice of interest and the corresponding slice comparable with each other. In response to information indicating that the user is observing the bone, the display processing unit 55 displays the slice of interest and a corresponding slice focusing on the bone in such a manner as to make the slice of interest and the corresponding slice comparable with each other. This process corresponds to an example of display control means for causing display means to display slice images that are associated with each other in such a manner as to make the associated slice images comparable with each other, on the basis of a selected piece of segment definition information.

The site of interest may be selected by a user designating a site of interest through the operation unit 35. Alternatively, the site of interest may be automatically selected in accordance with a display condition or the like for an image displayed on the display unit 36. Specifically, it can be determined that the user is observing the bone when display parameters for the image are related to a bone condition (parameters suitable for the observation of the bone), and that the user is observing the lung when display parameters for the image are related to the lung field condition (parameters suitable for the observation of the lungs). More specifically, a site of interest is estimated on the basis of a display condition for the image (the image I1) displayed on the display unit 36 in step S102. Examples of the display condition include set values such as window parameters for conversion of density values (e.g., a window level (WL) and a window width (WW)). Accordingly, a site of interest can be automatically selected. This process corresponds to an example of selection means for selecting one of a plurality of pieces of segment definition information in accordance with the region being observed by the user.

When a doctor performs diagnostic imaging to obtain a CT image, the doctor changes the window level (WL) or the window width (WW) depending on the site of the subject that is being observed by the doctor to change the setting of the display condition for an image of the site of the subject that is being observed by the doctor (i.e., convert density values in the displayed image). More specifically, for example, when the doctor performs diagnostic imaging of the bone, the window level (WL) is set to a value in the range of about 350 to 500 H.U., and the window width (WW) is set to a value in the range of about 1500 to 2500 H.U. Changing the setting of the display condition for an image depending on the site of the subject presents a displayed image having a density distribution to the doctor such that the site of the subject that is being observed by the doctor (e.g., the bone) is easily visible. Accordingly, a site (or an organ) being observed by the user, or the doctor, can be estimated from the set values of image display conditions (e.g., the window level (WL) and the window width (WW)) of the display unit 36 on which the images to be aligned (the images I1 to IN) are displayed. If a user interface (UI) is provided through which the user selects a preset value from among preset values set for display parameters, a site of interest can be assigned in advance to each of the preset values. Alternatively, a UI may be provided through which the user is able to set any desired display parameter. In this case, for example, a degree of coincidence between a display parameter suitable for the observation of each site and a display parameter set by the user may be determined, and the site for which the display parameter set by the user is the most suitable can be determined based on the degree of coincidence. For example, a rate of overlap between the range of a window suitable for the observation of each site and the range of a window set by the user is determined, and the obtained rates of overlap are compared to determine the site. Alternatively, the site may be determined on the basis of a distance between a window level determined in advance to be suitable for the observation of each site and a window level set by the user. The alignment unit 54 can select segment definition information including an anatomically characteristic cross section of a site being observed by the user from among a plurality of pieces of segment definition information created in advance on the basis of the estimation result, and switch corresponding slices in a plurality of images.

As described in the first and second modifications of the first embodiment, the coordinate value of a given slice in a reference coordinate system and corresponding slices of the given slice may be computed in advance and stored as auxiliary information of the given slice, and the auxiliary information may be read. That is, part of the processing of steps S103 to S105 is performed in advance to omit the computation to determine corresponding slices when displaying an image. Accordingly, the process of displaying corresponding slices may be speeded up.

The example described above provides a method of computing, for all of two or more pieces of segment definition information, coordinate values in the respective reference coordinate systems and corresponding slices. Alternatively, the computation described above may be performed only on a piece of information set in advance. For example, even when three or more pieces of segment definition information are preset, only a frequently used piece of information (such as the lung field condition or mediastinum condition) among them may be computed.

All the corresponding slices may be displayed side-by-side without performing a process of selecting and determining a site of interest. For example, in the example provided in this embodiment, with respect to a slice of interest in a certain image, both a corresponding slice focusing on the bone and a corresponding slice focusing on the lung may be displayed side-by-side. In this case, when a plurality of corresponding slices are substantially the same (the distance between the corresponding slices in the z direction is within a predetermined value), one of the corresponding slices may be displayed. When pieces of segment definition information related to three or more sites of interest are present, a plurality of sites of interest may be selected and respective corresponding slices may be displayed. For example, each of preset values of display parameters may be assigned a plurality of sites of interest in advance. Alternatively, a predetermined number of sites from the site with the highest degree of coincidence in display parameter may be selected as sites of interest. Alternatively, all the sites satisfying a predetermined condition (such as having a degree of coincidence in display parameter greater than or equal to a threshold) may be selected.

Further, a corresponding slice (default corresponding slice) available when no site of interest is determined may be calculated on the basis of corresponding slices of respective sites of interest, and may be displayed when no site of interest is determined. For example, a slice in the middle position of corresponding slices of respective sites of interest may be displayed as a default corresponding slice. Alternatively, any desired site may be defined in advance as a default site, and a corresponding slice of the site may be displayed. When no site of interest is determined, all the corresponding slices may be displayed.

In this embodiment, corresponding slices in a plurality of images can be switched and displayed in accordance with the site being observed by the user. Thus, advantageously, more sophisticated association can be provided.

Modifications

In the fourth embodiment, a belonging segment of each slice is determined for each of pieces of segment definition information corresponding to a plurality of sites of interest, and reference coordinate systems defined accordingly are used to determine corresponding slices in images. However, a corresponding slice determination method for associating a different slice in accordance with the site of interest is not limited to the method described in the first embodiment. Any other alternative means may be used for computation. For example, a plurality of three-dimensional images may be subjected to deformation alignment (estimation of a displacement field between images), and different corresponding slices may be set in accordance with the site of interest on the basis of the result. For example, when the focus is on a certain organ (e.g., the bone or lungs) is being observed, a displacement field in the organ region of a slice of interest may be used, and the slice that is the most similar to the displacement field may be defined and determined as a corresponding slice focusing on the organ. This method may be used to determine a corresponding slice that is different for each site of interest.

Other Embodiments

At least two of the plurality of modifications described above may be used in combination.

The disclosed technique may also provide embodiments of a system, an apparatus, a method, a program, a recording medium (storage medium), and the like, for example. Specifically, the disclosed technique may be applied to a system including a plurality of devices (such as a host computer, an interface device, an imaging device, and a web application) or may be applied to an apparatus including a single device.

It should be noted that one object of the present invention is achieved as follows: A recording medium (or a storage medium) having recorded thereon a program code (computer program) of software that implements the functions in the embodiments described above is supplied to a system or an apparatus. The storage medium is a computer-readable storage medium. The program code stored in the recording medium is read and executed by a computer (or a CPU or a microprocessing unit (MPU)) of the system or apparatus. In this case, the program code read from the recording medium implements the functions in the embodiments described above, and the recording medium having recorded thereon the program code provides an embodiment of the present invention.

The present invention is not limited to the embodiments described above, and can be changed and modified in various ways without departing from the spirit and scope thereof. Thus, the following claims are appended to make public the scope of the present invention.

According to the present invention, it is possible to provide accurate alignment using a reference coordinate system having coordinate values, each of which is related to an anatomical position.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An image processing apparatus comprising:
a memory storing a program; and
one or more processors which, by executing the program, function as:
an information obtaining unit configured to obtain segment definition information that defines a plurality of segments obtained by dividing a human body along a body axis;
an image obtaining unit configured to obtain a plurality of three-dimensional images, wherein each three-dimensional image, of the plurality of three-dimensional images, includes a respective plurality of slice images indicating cross sections of a subject;
a segment identifying unit configured to identify, based on the segment definition information, a segment to which a cross section corresponding to at least one slice image among the slice images included in the plurality of three-dimensional images belongs;
a coordinate value obtaining unit configured to obtain a coordinate value of the at least one slice image, based on the identified segment and a reference coordinate system in which a coordinate value is defined for each of the segments; and
an association unit configured to associate slice images having substantially a same coordinate value in the reference coordinate system, each of the slice images being included in the plurality of three-dimensional images.

2. The image processing apparatus according to claim 1, wherein the anatomically characteristic cross section comprises a cross section on which an anatomical feature at the boundary of the anatomical structure is delineated.

3. The image processing apparatus according to claim 1, wherein the one or more processors, by executing the program, further function as:
a display control unit for causing a display to display the associated slice images in such a manner as to make the associated slice images comparable with each other.

4. The image processing apparatus according to claim 1, wherein in response to obtaining the plurality of three-dimensional images, the segment identifying unit identifies segments to which cross sections corresponding to the at least one slice image in the plurality of three-dimensional images belong.

5. The image processing apparatus according to claim 1, wherein the information obtaining unit obtains a plurality of pieces of the segment definition information,
and
wherein the one or more processors, by executing the program, further function as:
an information association unit for associating, for each of the plurality of pieces of segment definition information, slice images indicating substantially a same position in the plurality of three-dimensional images;
a selection unit for selecting one of the plurality of pieces of segment definition information in accordance with a region being observed by a user; and
a display control unit for causing a display to display, based on the piece of segment definition information selected by the selection unit, the associated slice images in such a manner as to make the associated slice images comparable with each other.

6. The image processing apparatus according to claim 5, wherein the selection unit selects one of the plurality of pieces of segment definition information, based on a display condition in which the at least one of the plurality of three-dimensional images is displayed on the display.

7. The image processing apparatus according to claim 6, wherein the display condition at least includes a display parameter related to a density value of at least one of the plurality of three-dimensional images.

8. The image processing apparatus according to claim 5, wherein each of the plurality of pieces of segment definition information comprises segment definition information that is based on a different anatomical structure.

9. The image processing apparatus according to claim 1, wherein the one or more processors, by executing the program, further function as:
a position obtaining unit configured to obtain position information indicating a position of an anatomically characteristic cross section in the plurality of three-dimensional images, the anatomically characteristic cross section being a cross section on which a boundary of the anatomical structure is delineated,
wherein the segment identifying unit identifies the segment to which the cross section corresponding to the at least one slice image belongs, using the obtained position information of the anatomically characteristic cross section.

10. An image processing apparatus comprising:
a memory storing a program; and
one or more processors which, by executing the program, function as:

an information obtaining unit configured to obtain segment definition information that defines a plurality of segments obtained by dividing a human body along a body axis;
an image obtaining unit configured to obtain a plurality of three-dimensional images, where each three-dimensional image, of the plurality of three-dimensional images, includes a respective plurality of slice images indicating cross sections of a subject;
a segment identifying unit configured to identify, based on the segment definition information, a segment to which a cross section corresponding to at least one slice image among the slice images included in the plurality of three-dimensional images belongs;
a coordinate value obtaining unit configured to obtain a coordinate value of the at least one slice image, based on the identified segment and a reference coordinate system in which a coordinate value is defined for each of the segments;
an association unit configured to associate slice images having substantially a same coordinate value in the reference coordinate system, each of the slice images being included in the plurality of three-dimensional images; and
a position obtaining unit configured to obtain position information indicating a position of one or more anatomically characteristic cross sections of the subject, each of the one or more anatomically characteristic cross sections representing a boundary of one of the segments,
wherein the coordinate value obtaining unit obtains the coordinate value using the obtained position information, and
wherein the position obtaining unit estimates a position of an anatomically characteristic cross section of the subject outside an imaging range, the anatomically characteristic cross section being included in the plurality of three-dimensional images, among the one or more anatomically characteristic cross sections, to obtain position information indicating the position of the anatomically characteristic cross section outside the imaging range.

11. The image processing apparatus according to claim 1, wherein the one or more processors, by executing the program, further function as:
an alignment unit for aligning the plurality of three-dimensional images with a three-dimensional reference image including one or more slice images each associated with information on one of the segments,
wherein the segment identifying unit identifies, based on information on the segments associated with the one or more slice images included in the three-dimensional reference image aligned with the plurality of three-dimensional images, the segments to which the cross sections corresponding to the slice images included in the plurality of three-dimensional images belong.

12. An image processing method comprising:
obtaining segment definition information that defines a plurality of segments obtained by dividing a human body along a body axis;
obtaining a plurality of three-dimensional images, where in each three-dimensional image, of the plurality of three-dimensional images, includes a respective plurality of slice images indicating cross sections of a subject;
identifying, based on the segment definition information, a segment to which a cross section corresponding to at least one slice image among the slice images included in the plurality of three-dimensional images belongs;
obtaining a coordinate value of the at least one slice image, based on the identified segment and a reference coordinate system in which a coordinate value is defined for each of the segments;
associating slice images having substantially a same coordinate value in the reference coordinate system, each of the slice images being included in the plurality of three-dimensional images; and
obtaining position information indicating a position of an anatomically characteristic cross section in the plurality of three-dimensional images, the anatomically characteristic cross section being a cross section on which a boundary of an anatomical structure is delineated,
wherein the identifying identifies the segment to which the cross section corresponding to the at least one slice image belongs, using the obtained position information of the anatomically characteristic cross section.

13. An image processing method comprising:
obtaining segment definition information that defines a plurality of segments obtained by dividing a human body along a body axis;
obtaining a plurality of three-dimensional images, wherein each three-dimensional image, of the plurality of three-dimensional images, includes a respective plurality of slice images indicating cross sections of a subject;
identifying, based on the segment definition information, a segment to which a cross section corresponding to at least one slice image among the slice images included in the plurality of three-dimensional images belongs;
obtaining a coordinate value of the at least one slice image, based on the identified segment and a reference coordinate system in which a coordinate value is defined for each of the segments;
associating slice images having substantially a same coordinate value in the reference coordinate system, each of the slice images being included in the plurality of three-dimensional images; and
obtaining position information indicating a position of one or more anatomically characteristic cross sections of the subject, each of the one or more anatomically characteristic cross sections representing a boundary of one of the segments,
wherein the obtaining obtains the coordinate value using the obtained position information, and
wherein the obtaining estimates a position of an anatomically characteristic cross section of the subject outside an imaging range, the anatomically characteristic cross section being included in the plurality of three-dimensional images, among the one or more anatomically characteristic cross sections, to obtain position information indicating the position of the anatomically characteristic cross section outside the imaging range.

14. A non-transitory computer readable storage medium storing a program for causing an image processing apparatus to function as an apparatus comprising:
an information obtaining unit configured to obtain segment definition information that defines a plurality of segments obtained by dividing a human body along a body axis;
an image obtaining unit configured to obtain a plurality of three-dimensional images, wherein each three-dimensional image, of the plurality of three-dimensional images, includes a respective plurality of slice images indicating cross sections of a subject;

a segment identifying unit configured to identify, based on the segment definition information, a segment to which a cross section corresponding to at least one slice image among the slice images included in the plurality of three-dimensional images belongs;

a coordinate value obtaining unit configured to obtain a coordinate value of the at least one slice image, based on the identified segment and a reference coordinate system in which a coordinate value is defined for each of the segments;

an association unit configured to associate slice images having substantially a same coordinate value in the reference coordinate system, each of the slice images being included in the plurality of three-dimensional images; and a position obtaining unit configured to obtain position information indicating a position of an anatomically characteristic cross section in the plurality of three-dimensional images, the anatomically characteristic cross section being a cross section on which a boundary of an anatomical structure is delineated, wherein the segment identifying unit identifies the segment to which the cross section corresponding to the at least one slice image belongs, using the obtained position information of the anatomically characteristic cross section.

* * * * *